(12) United States Patent
Fuentes et al.

(10) Patent No.: US 9,587,218 B2
(45) Date of Patent: Mar. 7, 2017

(54) USE OF A CARBONACEOUS SUBSTITUTE FOR THE PRODUCTION OF YEAST

(71) Applicant: LESAFFRE ET COMPAGNIE, Paris (FR)

(72) Inventors: Jean-Luc Fuentes, Mouvaux (FR); Georges Rene Marcel Parasie, Sequedin (FR); Emmanuel Poilpre, Loudeac (FR); Anna-Dominique Quipourt-Isnard, Marcq-en-Baroeul (FR); Gilles George Albert Stien, Bourghelles (FR)

(73) Assignee: Lesaffre et Compagnie, Paris (FR)

( * ) Notice: Subject to any disclaimer, the term of this patent is extended or adjusted under 35 U.S.C. 154(b) by 390 days.

(21) Appl. No.: 14/303,884

(22) Filed: Jun. 13, 2014

(65) Prior Publication Data

US 2014/0342435 A1    Nov. 20, 2014

Related U.S. Application Data

(62) Division of application No. 12/922,317, filed as application No. PCT/IB2009/000511 on Mar. 13, 2009, now Pat. No. 8,790,908.

(30) Foreign Application Priority Data

Mar. 14, 2008  (FR) ..................................... 08 01398

(51) Int. Cl.
| | |
|---|---|
| C12N 1/32 | (2006.01) |
| C12N 1/20 | (2006.01) |
| C12N 1/00 | (2006.01) |
| C12N 1/18 | (2006.01) |
| C12N 1/38 | (2006.01) |
| C07K 14/395 | (2006.01) |
| C12N 1/16 | (2006.01) |
| C12R 1/865 | (2006.01) |
| C12N 15/01 | (2006.01) |

(52) U.S. Cl.
CPC .............. *C12N 1/38* (2013.01); *C07K 14/395* (2013.01); *C12N 1/16* (2013.01); *C12N 1/18* (2013.01); *C12N 1/32* (2013.01); *C12N 15/01* (2013.01); *C12R 1/865* (2013.01)

(58) Field of Classification Search
USPC ............................................... 435/255.2, 247
See application file for complete search history.

*Primary Examiner* — Maria Leavitt
(74) *Attorney, Agent, or Firm* — IP Attorneys Group, LLC

(57) ABSTRACT

The present invention relates to novel strains of *Saccharomyces* that can be produced on a carbonaceous substrate which makes it possible to completely and/or partially replace the use of sugar, and to the use thereof for the production of yeast, in particular on the industrial scale. The invention also relates to a method for producing yeast of the *Saccharomyces* genus on a carbonaceous substrate which makes it possible to completely or partially replace the use of sugar.

10 Claims, 5 Drawing Sheets

USE OF A CARBONACEOUS SUBSTITUTE FOR THE PRODUCTION OF YEAST

CROSS REFERENCE TO RELATED APPLICATIONS

This patent application is a divisional application of U.S. patent application Ser. No. 12/922,317 filed Sep. 13, 2010, now U.S. Pat. No. 8,790,908, titled "Use Of A Carbonaceous Substitute For The Production Of Yeast", which is the National Stage Entry of International. Patent Application PCT/IB2009/000511 filed Mar. 13, 2009. International Patent Application PCT/IB2009/000511 claims priority to French Patent Application 0801398 filed Mar. 14, 2008. Each of these applications is hereby incorporated by reference in its entirety.

TECHNICAL FIELD

The present invention relates to the production of yeasts, in particular on an industrial scale. A subject of the present invention is the use of a carbonaceous substrate making it possible to partially or totally replace the use of sugar for the production of yeasts, in particular on an industrial scale.

TECHNOLOGICAL BACKGROUND

The production of yeasts assumes the supply of different nutritive elements capable of ensuring their growth. These different nutritive elements are in particular carbon, nitrogen, phosphorus, sulphur, minerals and vitamins. Among the natural media which can be used for the production of yeast, molasses occupy a special position. In fact, molasses constitute a relatively complete medium capable of ensuring the supply of these nutritive elements. The average composition of the molasses is as follows: 66% to 73% sugars, 15% to 23% organic compounds and 10% to 12% mineral compounds (in percentages of total dry matter). The carbonaceous source provided by the molasses is essentially constituted by saccharose or sugars resulting from its hydrolysis (glucose and fructose).

However, the increased scarcity of cane and beet molasses, in particular linked to their extensive use for the production of bioethanol, jeopardizes this type of production. It is in particular necessary to find novel carbonaceous substrates to replace the saccharose provided by the molasses.

The production of yeasts can also be carried out on glucose or fructose syrups, for example obtained from the hydrolysis of starch and originating in particular from cereals (maize, wheat, rice) or potato. However, these syrups are relatively expensive and do not represent an economically profitable solution for replacing the saccharose of molasses within the context of industrial yeast production.

Yeast of the genus *Saccharomyces* is capable of synthesizing glycerol under anaerobiotic conditions or in a situation of severe stress, for example in the case of osmotic or thermal stress. The yeast *Saccharomyces* is moreover capable of degrading glycerol, but in a purely oxidative metabolism and in the absence of catabolic repression by sugars. Thus, the yeast *Saccharomyces*, placed in the presence of glycerol and sugar in a batch culture, is not capable of consuming the glycerol, while sugar remains in the medium.

Moreover, in an oxidative metabolism, the yeast *Saccharomyces* cultured on a carbonaceous substrate constituted solely by glycerol consumes the glycerol extremely slowly, which is not compatible with yeast production on an industrial scale. (Lages and Lucas, 1997, Biochimica and Biophysica Acta).

There is therefore a real need for novel strains for the production of yeasts which make it possible to totally or partially replace sugar as a carbonaceous substrate, with yeast production yields compatible with economic and industrial exploitation, and/or without loss in quality of the yeasts produced.

SUMMARY OF THE INVENTION

A subject of the present invention is to provide novel strains of *Saccharomyces* capable of being produced on a carbonaceous substrate making it possible to totally and/or partially replace the use of sugar.

A subject of the invention is also the use of these strains for the production of yeasts, in particular on an industrial scale.

Another subject of the invention relates to a method for the production of yeasts of the genus *Saccharomyces* on a carbonaceous substrate making it possible to totally or partially replace the use of sugar, said method also making it possible to obtain a yield similar to that of a production on a sugar-type substrate and/or making it possible to obtain yeasts of similar quality.

A subject of the present invention is a strain of *Saccharomyces*, characterized in that in the presence of a culture medium comprising a mixture of glycerol and sugar, under aerobic conditions, it consumes at least 80% of the glycerol in said mixture, said mixture comprising a proportion of glycerol of at least 20% as saccharose equivalent, the sum of the proportions of glycerol and sugar in said mixture being equal to 100% as saccharose equivalent.

A subject of the present invention is also a strain as defined above, characterized in that it consumes at least 85% of the glycerol in the mixture, preferably at least 90% of the glycerol in the mixture, more preferentially at least 95% of the glycerol in the mixture, even more preferentially at least 98% of the glycerol in the mixture.

A subject of the present invention is also a strain as defined above, characterized in that said mixture comprises a proportion of glycerol of at least 30% as saccharose equivalent, preferably at least 40% as saccharose equivalent, more preferentially at least 50% as saccharose equivalent, even more preferentially at least 60% as saccharose equivalent, even more preferentially at least 70% as saccharose equivalent, even more preferentially at least 80% as saccharose equivalent even more preferentially at least 90% as saccharose equivalent.

The present invention relates in particular to a strain as defined above, characterized in that it is chosen from the species *cerevisiae, boulardii, carlsbergensis* and *uvarum*.

A subject of the present invention is a strain as defined above, characterized in that it is chosen from a natural variant and/or a genetically modified strain.

A particular subject of the present invention is a strain as defined above, characterized in that it is chosen from the strain deposited with the CNCM on 20 Dec. 2007 under number CNCM I-3886, the strain deposited with the CNCM on 20 Dec. 2007 under number CNCM I-3887, the strain deposited with the CNCM on 20 Dec. 2007 under number CNCM I-3888, the strain deposited with the CNCM on 3 Mar. 2009 under number I-4132 and the strain deposited with the CNCM on 3 Mar. 2009 under number I-4133.

A particular subject of the present invention is a strain as defined above, characterized in that it is chosen from
the strain deposited with the CNCM on 3 Mar. 2009 under number I-4129,
the strain deposited with the CNCM on 3 Mar. 2009 under number I-4130 and
the strain deposited with the CNCM on 3 Mar. 2009 under number I-4131.

Legal deposit under the regulations of the Budapest Treaty were made of the *Saccharomyces cerevisiae* strains CNCM I-3886, CNCM I-3887, CNCM I-3888 on Dec. 20, 2007 and *Saccharomyces cerevisiae* strains CNCM-I-4129, CNCM-I-4130, CNCM-I-4131, CNCM-I-4132, CNCM-I-4133 and CNCM-I-4133 on Mar. 3, 2009 at the Lesaffre et Compagnie, 75001 Paris.

A subject of the present invention is also the use of a strain as defined above for the production of yeasts in the presence of a mixture of glycerol and sugar comprising a proportion of glycerol of at least 5% as saccharose equivalent, the sum of the proportions of glycerol and sugar in said mixture being equal to 100% as saccharose equivalent.

A subject of the present invention is the use of a mixture of glycerol and sugar for the production of yeasts from at least one strain of *Saccharomyces*, characterized in that said strain consumes at least 80% of the glycerol in said mixture, said mixture comprising a proportion of glycerol of at least 5% as saccharose equivalent, the sum of the proportions of glycerol and sugar in said mixture being equal to 100% as saccharose equivalent.

A subject of the present invention is also a method for the production of yeasts comprising the stages of:
introduction of a strain of yeast of the genus *Saccharomyces* into a fermenter, and
multiplication of said strain under aerobic conditions in a culture medium comprising a mixture of glycerol and sugar, said mixture comprising a proportion of glycerol of at least 5% as saccharose equivalent, the sum of the proportions of glycerol and sugar in said mixture being equal to 100% as saccharose equivalent.

A particular subject of the present invention is a method as defined above, characterized in that at least 80% of the glycerol in said mixture is consumed by said strain, preferably at least 85% of the glycerol in said mixture, more preferentially at least 90% of the glycerol in said mixture, even more preferentially at least 95% of the glycerol in said mixture, even more preferentially at least 98% of the glycerol in said mixture.

A subject of the present invention is a method as defined above, characterized in that the multiplication of said strain is carried out according to a semi-continuous mode or according to a continuous mode.

A subject of the present invention is also a method as defined above, characterized in that said mixture comprises a proportion of glycerol of at least 8% as saccharose equivalent, preferably at least 10% as saccharose equivalent, more preferentially at least 12% as saccharose equivalent, even more preferentially at least 15% as saccharose equivalent, even more preferentially at least 17% as saccharose equivalent, even more preferentially at least 20% as saccharose equivalent.

A particular subject of the present invention is a method as defined above, characterized in that said mixture comprises a proportion of glycerol of at least 30% as saccharose equivalent.

A subject of the present invention is a method as defined above, characterized in that said mixture comprises a proportion of glycerol of at least 40% as saccharose equivalent, preferably at least 50% as saccharose equivalent, more preferentially at least 60% as saccharose equivalent, even more preferentially at least 70% as saccharose equivalent, even more preferentially at least 80% as saccharose equivalent, even more preferentially at least 90% as saccharose equivalent.

A subject of the present invention is a method as defined above, characterized in that said strain of yeast is a strain as defined above.

DETAILED DESCRIPTION OF THE INVENTION

Figure 1:
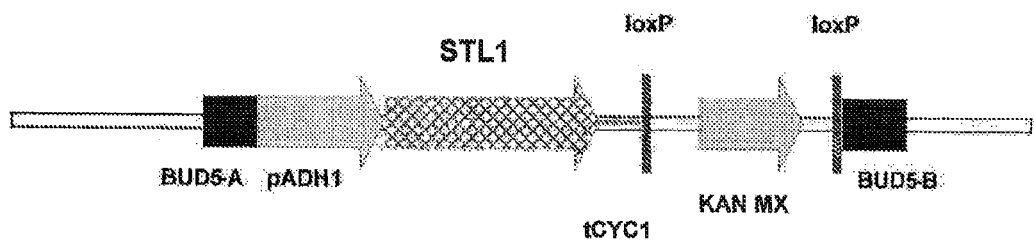
FIG. 1: Diagram of the expression cassette used for integrating the STL1 gene into the genome of strains of yeasts.
The STL1 gene is under the control of the pADH1 promoter and it is followed by the CYC1 terminator of yeast. Two recombinogenic fragments (BUD5-A and BUD5-B) each of 500 nucleotides frame the expression cassette, in order to ensure the insertion by homologous recombination of the cassette into the yeast genome, after transformation, at the BUD5 locus (YCR038c) located on the chromosome III. The gene conferring resistance to KANMX geneticin is inserted downstream of the STL1 gene, framed by two loxP sites.

A subject of the present invention is a strain of *Saccharomyces*, characterized in that in the presence of a culture medium comprising a mixture of glycerol and sugar, under aerobic conditions, it consumes at least 80% of the glycerol in said mixture, said mixture comprising a proportion of glycerol of at least 20% as saccharose equivalent, the sum of the proportions of glycerol and sugar in said mixture being equal to 100% as saccharose equivalent.

Surprisingly and unexpectedly, the Inventors obtained *Saccharomyces* yeast strains capable of consuming at least 80% of the glycerol in a mixture of glycerol and sugar, simultaneously to their consumption of sugar, under aerobic conditions, in a semi-continuous or continuous culture.

The Inventors have in fact shown that standard industrial baking yeasts, such as the strains deposited at the NCYC (National Collection of Yeast Cultures) under numbers NCYC995 and NCYC996, consume glycerol only partially in the presence of a mixture of glycerol and sugar in semi-continuous culture and/or in continuous culture (see Example 2). At the end of the culture, the culture medium which is free from yeasts then contains a large residual quantity of glycerol which has accumulated during the culture.

The strains according to the invention are characterized by the fact that in the presence of a culture medium comprising a mixture of glycerol and sugar, they consume at least 80% of the glycerol in said mixture, the percentage being given in weight/weight. In other words, the strain according to the invention consumes at least 80% of the total mass of glycerol present in the mixture of glycerol and sugar.

A particular subject of the present invention is a strain of *Saccharomyces*, characterized in that in the presence of a culture medium comprising a mixture of glycerol and sugar, under aerobic conditions, it consumes at least 80% of the glycerol in said mixture, said mixture comprising a proportion of glycerol of 20% as saccharose equivalent, the sum of the proportions of glycerol and sugar in said mixture being equal to 100% as saccharose equivalent.

The determination of the consumption of glycerol can be carried out by measuring the residual quantity of glycerol in the culture medium, after a semi-continuous culture, or by measuring the residual quantity of glycerol in the medium drawn off in the case of a continuous culture.

In the case of a semi-continuous culture, the measurement of the residual quantity of glycerol in the culture medium is carried out at the end of the culture.

By "end of the culture" is meant the moment when the feed of sugar is stopped.

The duration of the culture is in particular less than or equal to the duration of a culture of the same strain on a mixture comprising 100% sugar as saccharose equivalent.

The duration of the culture is in particular less than 24 hours.

The duration of the culture is in particular less than 20 hours.

The duration of the culture is for example 22 hours.

In the case of a continuous culture, the residual quantity of glycerol is measured at any moment, once the steady state is reached.

The steady state is reached when the concentrations in the fermenter are stable for at least 3 residence times, the residence time being the ratio 1/[dilution rate].

Conventionally, the culture conditions are such that the metabolism of the strain of yeast is essentially respiratory and/or such that there is essentially no production of ethanol.

The word "essentially" means that these conditions are satisfied over the total duration of the culture, but that it is possible that from time to time, these conditions are not satisfied in semi-continuous mode, for example during the first hours of the culture, in particular for a duration comprised between ¼ and ⅓ of the culture duration, and in particular during the first 5 hours of a culture in semi-continuous mode.

In a chemostat mode, the culture conditions are such that the metabolism of the strain of yeast is respiratory and/or such that there is no production of ethanol when the steady state is reached.

The expression "the metabolism of the strain of yeast is essentially respiratory" means that the carbon is oxidized, and not fermented, over the total duration of the culture, part of the carbon being able to be fermented in a temporary manner.

The expression "there is essentially no production of ethanol" means that the concentration of ethanol at the end of the culture is less than 1%, preferably less than 0.1%, more preferentially less than 0.01%, more preferentially less than 0.001%.

A person skilled in the art knows how to adjust the parameters for culture of a given strain of yeast, in order that the culture conditions are such that the metabolism of said strain is essentially respiratory and/or such that there is essentially no production of ethanol.

The residual quantity of glycerol is preferably measured in the culture medium which is free from yeasts.

The residual quantity of glycerol in the culture medium is for example measured by HPLC or GC chromatography, enzymatic assay or any other appropriate method.

The strains of yeast according to the invention are therefore particularly useful, as they are capable of consuming glycerol continuously, over a production period compatible with industrial exploitation.

The expression "capable of consuming glycerol continuously" means that there is essentially no accumulation of glycerol over the total duration of the culture, but that from time to time accumulation remains possible if the metabolism of the yeast is not essentially respiratory and/or if there is a production of alcohol.

By the expression "mixture of glycerol and sugar", is meant a mixture constituted by glycerol and sugar in variable proportions, the sum of the proportions of glycerol and sugar in said mixture being equal to 100% as saccharose equivalent.

The mixture of glycerol and sugar constitutes the only source of sugar and glycerol in the culture medium.

The mixture of glycerol and sugar is, preferably, prepared before its introduction into the culture medium.

Glycerol, also called glycerine or propan-1,2,3-triol is a polyol. Pure glycerol is presented in the form of a transparent and viscous liquid and it is soluble in water.

The glycerol according to the invention can be used in the pure form and/or in the form of a product containing glycerol, and/or be supplied in any form capable of producing glycerol.

The sugar is preferably a sugar which can be immediately assimilated by the yeast, in particular a simple sugar of glucose, fructose or saccharose type, and/or a mixture of these sugars.

The sugar can be supplied in the form of glucose syrups and/or fructose syrups and/or starch hydrolysates and/or in the form of molasses and/or in the form of a substance capable of producing sugars which can be assimilated by the strain of yeast and/or in the form of a mixture thereof.

The sugar is preferably supplied in the form of molasses.

The mixture of glycerol and sugar constitutes at least 90% of the carbon source for the yeast, preferably at least 95% of the carbon source, more preferentially at least 98% of the carbon source. The carbonaceous source in the culture medium, other than the mixture of glycerol and sugar, comprises for example amino acids, lipids, organic acids naturally present in molasses or crude hydrolysates of agricultural origin.

The expression "the sum of the proportions of glycerol and sugar in said mixture being equal to 100% as saccharose equivalent" means that when the proportion of glycerol expressed as saccharose equivalent is x %, the proportion of sugar in the mixture expressed as saccharose equivalent is (100−x) %.

The equivalence is determined here with respect to glycolytic metabolism, according to which one mole of saccharose is converted to one mole of fructose and one mole of glucose which are themselves converted to four moles of pyruvate (cf. Principes de la Biochimie, Lehninger, 1994).

One mole of glucose is therefore converted to two moles of pyruvate and one mole of fructose to two moles of pyruvate.

According to this same metabolism, one mole of glycerol is converted into one mole of pyruvate.

Thus, four moles of glycerol correspond to one mole of saccharose equivalent.

Two moles of glucose correspond to one mole of saccharose equivalent.

Two moles of fructose correspond to one mole of saccharose equivalent.

1.076 g of glycerol correspond here to one gram of saccharose equivalent.

For example, a kilogram of a mixture finally containing 250 g/kg of saccharose equivalent and a proportion of 20% glycerol as saccharose equivalent is therefore constituted by 50 g of saccharose equivalent in the form of glycerol and 200 g of saccharose equivalent in the form of sugar. Given crude molasses having a sugar content of 500 g/kg as saccharose equivalent, for preparing a kilogram of this mixture, firstly 50×1.076 g=54 g of pure glycerol (which corresponds to 50 g of saccharose equivalent in the form of glycerol) and 400 g of said crude molasses (which corresponds to 200 g of saccharose equivalent in the form of sugar) are mixed, then pure water is added to reach a final mass of mixture of 1 kilogram.

The culture medium is here called fresh culture medium when it has not been placed in the presence of strains of yeast.

The culture medium is here called reaction medium when it has been placed in the presence of strains of yeast.

The strain of yeast according to the invention is placed in the presence of the culture medium under aerobic conditions.

Preferably, the strain of yeast according to the invention is placed in the presence of the culture medium in a fermenter suitable for the production of yeast. The volume of the fermenter can vary from a few milliliters to several cubic meters.

The fermenter is also called a reactor hereafter.

The fermenter is preferably suitable for a culture under aerobic conditions.

The strain of yeast is preferably placed in the presence of the culture medium within the context of a culture in semi-continuous mode and/or in continuous mode.

By the expression "culture in semi-continuous mode" or "semi-continuous culture" or "semi-continuous mode", also called "fed-batch", is meant here a culture in a fermenter which is fed progressively by the culture medium, but no volume of medium of which is drawn off. In such a method, the volume of culture is variable (and generally increasing) in the fermenter. The feed rate in a culture in semi-continuous mode is constant or variable.

One example of semi-continuous culture is a culture carried out under the conditions described in the reference book "Yeast Technology", Chapter 6, 2nd edition, 1991, G. Reed and T. W. Nagodawithana, published by Van Nostrand Reinhold, ISBN 0-442-31892-8.

By the expression "culture in continuous mode" or "continuous culture" or "continuous mode", is meant here a culture in a fermenter during which the fermenter is fed with fresh culture medium and in which part of the reaction medium is drawn off. In a culture in continuous mode, the volume of culture in the fermenter is variable or constant.

According to a particular embodiment of the culture in continuous mode, the feed rate and the draw-off rate are equal.

One example of continuous culture is a culture carried out under the conditions described in the reference book "Yeast Technology", Chapter 6, 2nd edition, 1991, G. Reed and T. W. Nagodawithana, published by Van Nostrand Reinhold, ISBN 0-442-31892-8.

The culture in chemostat mode is a particular form of continuous culture.

In a culture in chemostat mode, the different parameters such as the dissolved oxygen level, nutrient concentrations, pH, cell density, are kept constant.

The culture medium comprises as constituents the mixture of glycerol and sugar and the other elements necessary for the growth of the yeasts.

The other elements necessary for the growth of the yeasts are the following: at least one source of nitrogen, at least one source of sulphur, at least one source of phosphorus, at least one source of vitamins and/or at least one source of minerals.

These other elements are supplied in sufficient quantities so as not to constitute a factor limiting the growth of the yeasts and in order to maintain an essentially respiratory metabolism.

The source of nitrogen is for example supplied in the form of ammonium sulphate, ammonium hydroxide, di-ammonium phosphate, ammonia, urea and/or a combination thereof.

The source of sulphur is for example supplied in the form of ammonium sulphate, magnesium sulphate, sulphuric acid and/or a combination thereof.

The source of phosphorus is for example supplied in the form of phosphoric acid, potassium phosphate, di-ammonium phosphate, mono-ammonium phosphate, and/or a combination thereof.

The source of vitamins is for example supplied in the form of molasses, yeast hydrolysate, pure vitamin solution or a mixture of pure vitamins and/or a combination thereof.

The source of vitamins supplies all of the vitamins to the yeast in quantities at least equivalent to those recommended in the reference works. Several sources of vitamins can be combined.

The source of minerals is for example supplied in the form of molasses, a mixture of mineral salts and/or a combination thereof.

The source of minerals supplies all of the macroelements and trace elements to the yeast in quantities at least equivalent to those recommended in the reference works. Several sources of minerals can be combined.

The same substance can supply several different elements.

The strains of yeast according to the invention are in particular chosen from the strains making it possible to produce breadmaking yeast, brewer's yeast, wine-making yeast, yeast for the production of alcohol, and/or yeast for the production of recombinant proteins, for example for the production of therapeutic proteins.

The glycerol consumption of a strain of *Saccharomyces* can, for example, be measured under the conditions described in Example 2, in order to determine whether said strain, in the presence of a culture medium comprising a mixture of glycerol and sugar, under aerobic conditions, consumes at least 80% of the glycerol in the mixture, said mixture comprising a proportion of glycerol of 20% as saccharose equivalent, the sum of the proportions of glycerol and sugar in said mixture being equal to 100% as saccharose equivalent.

A subject of the present invention is also a strain of *Saccharomyces*, characterized in that in the presence of a culture medium comprising a mixture of glycerol and sugar, under aerobic conditions, it consumes at least 80% of the glycerol in said mixture, said mixture comprising a proportion of glycerol of 30% as saccharose equivalent, the sum of the proportions of glycerol and sugar in said mixture being equal to 100% as saccharose equivalent.

A subject of the present invention is also a strain of *Saccharomyces*, characterized in that in the presence of a culture medium comprising a mixture of glycerol and sugar, under aerobic conditions, it consumes at least 80% of the glycerol in said mixture, said mixture comprising a proportion of glycerol of 40% as saccharose equivalent, the sum of the proportions of glycerol and sugar in said mixture being equal to 100% as saccharose equivalent.

A particular subject of the present invention is a strain as defined above, characterized in that it consumes at least 85% of the glycerol in the mixture, preferably at least 90% of the glycerol in the mixture, more preferentially at least 95% of the glycerol in the mixture, even more preferentially at least 98% of the glycerol in the mixture.

A particular subject of the present invention is a strain as defined above, characterized in that said mixture comprises a proportion of glycerol of at least 30% as saccharose equivalent, preferably at least 40% as saccharose equivalent, more preferentially at least 50% as saccharose equivalent, even more preferentially at least 60% as saccharose equivalent, even more preferentially at least 70% as saccharose equivalent, even more preferentially at least 80% as saccharose equivalent, even more preferentially at least 90% as saccharose equivalent.

A subject of the present invention is also a strain as defined above, characterized in that the proportion of glycerol in said mixture is at most 95% as saccharose equivalent, preferably at most 90% as saccharose equivalent, more preferentially at most 85% as saccharose equivalent.

A particular subject of the present invention is a strain as defined above, characterized in that the proportion of glycerol in said mixture is from 20% to 90% as saccharose equivalent, preferably 20% to 80% as saccharose equivalent, more preferentially 30% to 70% as saccharose equivalent, even more preferentially 30% to 60% as saccharose equivalent.

A subject of the present invention is a strain as defined above, characterized in that it is chosen from the species cerevisiae, boulardii, carlsbergensis and uvarum.

A preferred strain according to the invention is a strain of Saccharomyces cerevisiae.

A subject of the present invention is a strain as defined above, characterized in that it is chosen from a natural variant and/or a genetically modified strain.

The term "natural variant" here denotes a strain obtained by crossing and/or hybridization of strains of yeast and/or obtained by spontaneous mutation and/or by random mutagenesis, for example following exposure to stress conditions, to a UV treatment or to a treatment with mutagenic agents.

The gene pool of a natural variant has not been modified by genetic engineering.

Two methods of random mutagenesis can for example be used in order to obtain natural variants according to the invention (see also Example 3 below).

The first method consists of a selection of the natural variants on the basis of their glycerol consumption and of their yield, directly after an exposure to UV radiation followed by isolation of clones.

The second method comprises:
a first stage of exposure to UV radiation,
a second stage of culture in chemostat mode in the presence of a mixture of sugar and glycerol,
a third stage of isolation of clones, and
a fourth stage of selection of the natural variants on the basis of their consumption of glycerol and of their yield.

This second method makes it possible to enrich the culture with natural variants consuming glycerol in the presence of sugar, before commencing the selection stage.

A particular subject of the invention is thus the strain deposited with the CNCM on 3 Mar. 2009 under number CNCM I-4129, the strain deposited with the CNCM on 3 Mar. 2009 under number CNCM I-4130 and the strain deposited with the CNCM on 3 Mar. 2009 under number CNCM I-4131.

These three strains have been obtained by random mutagenesis following a UV treatment and selection on the basis of their consumption of glycerol and their yield (see Example 3).

A subject of the present invention is a natural variant as defined above, characterized in that it is strain number CNCM I-4129.

In semi-continuous culture, in a culture medium containing a mixture of glycerol and sugar with a proportion of glycerol of 20% as saccharose equivalent, the strain of yeast CNCM I-4129 consumes more than 95% of the glycerol in the mixture.

In continuous culture, in a culture medium containing a mixture of glycerol and sugar, the strain of yeast CNCM I-4129 consumes more than 80% of the glycerol in the mixture, when the proportion of glycerol in said mixture varies from 20% to 50%.

A subject of the present invention is a natural variant as defined above, characterized in that it is strain number CNCM I-4130.

In semi-continuous culture, in a culture medium containing a mixture of glycerol and sugar with a proportion of glycerol of 20% as saccharose equivalent, the strain of yeast CNCM I-4130 consumes more than 95% of the glycerol in the mixture.

In continuous culture, in a culture medium containing a mixture of glycerol and sugar, the strain of yeast CNCM I-4130 consumes more than 80% of the glycerol in the mixture, when the proportion of glycerol in said mixture varies from 20% to 50%.

A subject of the present invention is a natural variant as defined above, characterized in that it is strain number CNCM I-4131.

In semi-continuous culture, in a culture medium containing a mixture of glycerol and sugar with a proportion of glycerol of 20% as saccharose equivalent, the strain of yeast CNCM I-4131 consumes more than 95% of the glycerol in the mixture.

In continuous culture, in a culture medium containing a mixture of glycerol and sugar, the strain of yeast CNCM I-4131 consumes more than 80% of the glycerol in the mixture, when the proportion of glycerol in said mixture varies from 20% to 50%.

By the expression "genetically modified strain" or GMO strain, is meant a strain the gene pool of which has been modified by genetic engineering.

A genetically modified strain can have undergone a modification of its endogenous DNA, for example by a point mutation, partial or total, of a gene. The mutation can consist of an insertion, deletion and/or substitution of at least one nucleotide.

The mutation preferably induces a modification of the product of the gene after transcription and/or translation. The mutation can in particular lead to a truncation of the product of the gene, a modification of at least one amino acid in the sequence of the product of the gene and/or a reading frame shift during the transcription.

A genetically modified strain can comprise an exogenous DNA, integrated or not into at least one chromosome of the yeast and/or into at least one plasmid of the yeast.

A preferred genetically modified strain comprises an exogenous DNA integrated into at least one chromosome of the yeast.

The exogenous DNA can be a fragment of DNA,—for example a gene fragment, a complete or partial expression cassette—, and/or a plasmid.

When the genetically modified strain comprises an integrated exogenous DNA, it is a single integration or multi-copy integration.

A subject of the present invention is a strain as defined above, characterized in that it is a strain genetically modified at the level of at least one gene involved in at least one metabolic route of the glycerol.

A subject of the present invention is a strain as defined above, characterized in that it is a strain genetically modified at the level of at least one gene involved in the catabolism of the glycerol or in the regulation of the catabolism of the glycerol.

A more particular subject of the present invention is a strain as defined above, characterized in that it is a strain genetically modified at the level of at least one gene chosen from the STL1, GUP1, GUP2, GUT1, GUT2, FPS1 and/or ADR1 genes and/or a gene involved in the repression by glucose and/or of a combination thereof.

A genetically modified strain according to the invention exhibits in particular an increase in the expression of a gene and/or a reduction in the expression of a gene and/or a constitutive expression and/or a differential expression of a gene, and/or the expression of a gene absent from the original strain of yeast.

A more particular subject of the present invention is a strain as defined above, characterized in that it is a strain genetically modified at the level of at least one gene chosen from the STL1, GUP1, GUP2, GUT1, GUT2 genes and/or of a combination thereof.

The modification of the strains according to the invention is carried out using the technique well known to a person skilled in the art (see Molecular Cloning, 3rd edition, Sambrook and Russel).

A genetically modified strain of yeast according to the invention preferably consumes more than 90% of the glycerol in the mixture of glycerol and sugar.

The STL1 gene encodes the glycerol permease which in particular allows the glycerol to enter the cell.

A strain according to the invention genetically modified at the level of the STL1 gene expresses the STL1 gene in the presence of sugar.

A preferred strain genetically modified at the level of the STL1 gene according to the invention overexpresses the STL1 gene in the presence of sugar compared with the corresponding non-mutated strain.

The STL1 gene in the genetically modified strain according to the invention is for example placed under the control of a constitutive promoter or of a promoter induced by glucose.

A preferred strain genetically modified at the level of the STL1 gene according to the invention has an STL1 gene transcription rate multiplied at least by 100 in relation to that of the corresponding non-mutated strain, preferably multiplied at least by 200, more preferentially at least by 250, the transcription rate being calculated after quantitative PCR on cDNA obtained by reverse transcription.

The GUP1 gene codes for a membrane protein involved in the active transport of the glycerol in the cell.

A strain according to the invention genetically modified at the level of GUP1 expresses the GUP1 gene in the presence of sugar.

The GUP2 gene codes for a membrane protein involved in the active transport of the glycerol in the cell.

A strain according to the invention genetically modified at the level of GUP2 expresses the GUP2 gene in the presence of sugar.

The FPS1 or YLL043W gene codes for a transport membrane protein allowing in particular the export of the glycerol.

A strain according to the invention genetically modified at the level of FPS 1 does not express the FPS1 gene, for example following deletion of the gene.

The ADR1 or YDR216W gene codes for a transcription activator involved in the expression of genes involved in the routes of use of ethanol, glycerol and fatty acids. Such genes are in particular regulated by glucose repression.

A strain according to the invention genetically modified at the level of ADR1 expresses the ADR1 gene in the presence of sugar.

The GUT1 or YHL032C gene codes for a glycerol kinase which converts glycerol to glycerol-3-phosphate.

A strain according to the invention genetically modified at the level of GUT1 expresses the GUT1 gene in the presence of sugar.

The GUT2 or YIL155C gene codes for glycerol-3-phosphate dehydrogenase which converts glycerol-3-phosphate to DHAP (dihydroxyacetone-phosphate).

A strain according to the invention genetically modified at the level of GUT2 expresses the GUT2 gene in the presence of sugar.

A strain according to the invention is for example modified by conversion with an expression cassette allowing the expression of a gene as defined above, in particular in the presence of sugar.

The expression cassette comprises a promoter, a gene of interest and a terminator. The terminator is an artificial sequence or a yeast termination sequence.

The promoter is a constitutive or inducible promoter.

A preferred promoter according to the invention is the glucose-inducible pADH1 promoter.

A subject of the present invention is a strain as defined above, characterized in that it is the strain deposited with the CNCM on 20 Dec. 2007 under number CNCM I-3886.

Figure 2:
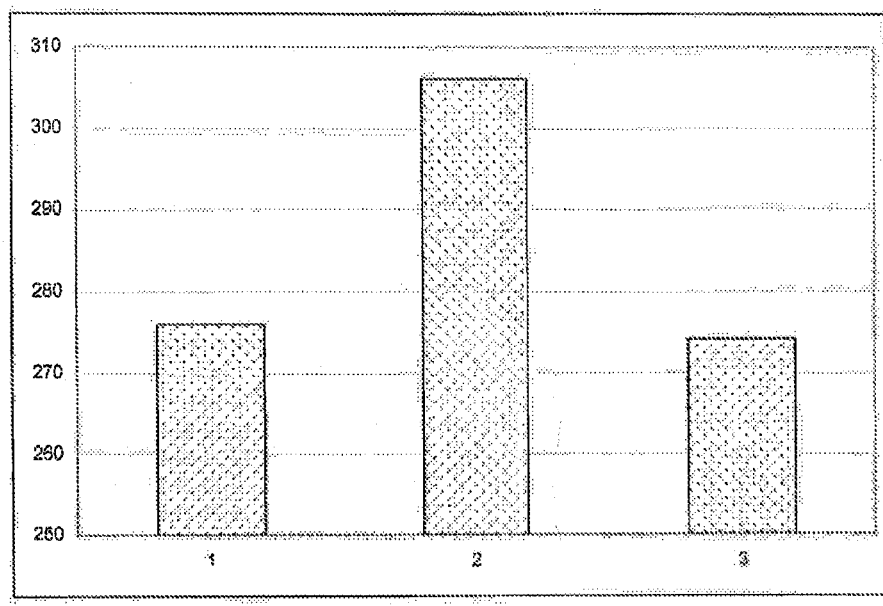
FIG. 2: Level of expression of the STL1 gene in the strains genetically modified for expressing the STL1 gene, after culture in the presence of sugar.
The graph represents the ratio of the level of mRNA of mutated strain of yeasts expressing the STL1 gene to the level of mRNA of the corresponding non-mutated strain (on the y-axis).
  1: ratio of the level of mRNA of the strain deposited at the CNCM under number I-3887 to that of the non-mutated strain NCYC 996;
  2: ratio of the level of mRNA of the strain deposited at the CNCM under number I-3888 to that of the non-mutated strain NCYC 995;
  3: ratio of the level of mRNA of the strain deposited at the CNCM under number I-3886 to that of the non-mutated strain I-3399.

Strain of yeast number CNCM I-3886 was obtained by integration of the expression cassette represented in FIG. 2 in the genome of the strain deposited at the CNCM under number CNCM I-3399.

Strain of yeast number CNCM I-3886 strongly expresses the STL1 gene in the presence of sugar (mRNA level more than 270 times greater than that of the non-mutated strain I-3399).

In semi-continuous culture, in a culture medium containing a mixture of glycerol and sugar with a proportion of glycerol of 20% as saccharose equivalent, the strain of yeast CNCM I-3886 consumes more than 95% of the glycerol in the mixture.

In continuous culture, in a culture medium containing a mixture of glycerol and sugar, the strain of yeast CNCM I-3886 consumes more than 90% of the glycerol in the mixture, when the proportion of glycerol in said mixture varies from 20% to 80%.

A subject of the present invention is a strain as defined above, characterized in that it is the strain deposited with the CNCM on 20 Dec. 2007 under number CNCM I-3887.

Strain of yeast number CNCM I-3887 was obtained by integration of the expression cassette represented in FIG. 2 in the genome of the strain deposited at the NCYC (National Collection of Yeast Cultures) under number NCYC 996.

Strain of yeast number CNCM I-3887 strongly expresses the STL1 gene in the presence of sugar (mRNA level more than 270 times greater than that of the non-mutated strain NCYC 996).

In semi-continuous culture, in a culture medium containing a mixture of glycerol and sugar with a proportion of glycerol of 20% as saccharose equivalent, the strain of yeast CNCM I-3887 consumes more than 95% of the glycerol in the mixture.

In continuous culture, in a culture medium containing a mixture of glycerol and sugar, the strain of yeast CNCM I-3887 consumes more than 90% of the glycerol in the mixture, when the proportion of glycerol in said mixture varies from 20% to 80%.

A subject of the present invention is a strain as defined above, characterized in that it is the strain deposited with the CNCM on 20 Dec. 2007 under number CNCM I-3888.

Strain of yeast number CNCM I-3888 was obtained by integration of the expression cassette represented in FIG. 2 in the genome of the strain deposited at the NCYC (National Collection of Yeast Cultures) under number NCYC 995.

Strain of yeast number CNCM I-3888 therefore strongly expresses the STL1 gene in the presence of sugar (mRNA level more than 300 times greater than that of the non-mutated strain NCYC 995).

In semi-continuous culture, in a culture medium containing a mixture of glycerol and sugar with a proportion of glycerol of 20% as saccharose equivalent, the strain of yeast CNCM I-3888 consumes more than 95% of the glycerol in the mixture.

In continuous culture, in a culture medium containing a mixture of glycerol and sugar, the strain of yeast CNCM I-3888 consumes more than 90% of the glycerol in the mixture, when the proportion of glycerol in said mixture varies from 20% to 80%.

A subject of the present invention is a strain as defined above, characterized in that it is the strain deposited with the CNCM on 3 Mar. 2009 under number CNCM I-4132.

Strain of yeast number CNCM I-3886 was obtained by integration of the expression cassette represented in FIG. 2 in the genome of the strain deposited at the CNCM under number CNCM I-3399.

Strain of yeast number CNCM I-4132 therefore strongly expresses the STL1 gene in the presence of sugar (mRNA level more than 200 times greater than that of the non-mutated strain I-4072).

In semi-continuous culture, in a culture medium containing a mixture of glycerol and sugar with a proportion of glycerol of 20% as saccharose equivalent, the strain of yeast CNCM I-4132 consumes more than 80% of the glycerol in the mixture.

A subject of the present invention is a strain as defined above, characterized in that it is the strain deposited with the CNCM on 3 Mar. 2009 under number CNCM I-4133.

The strain of yeast CNCM I-4133 was obtained by integration of the expression cassette represented in FIG. 2 in the genome of the strain deposited with the CNCM on 4 Sep. 2008 under number I-4071.

Strain of yeast number CNCM I-4133 expresses the STL1 gene strongly in the presence of sugar (mRNA level more than 200 times greater than that of the non-mutated strain I-4071).

In semi-continuous culture, in a culture medium containing a mixture of glycerol and sugar with a proportion of glycerol of 20% as saccharose equivalent, the strain of yeast CNCM I-4133 consumes more than 80% of the glycerol in the mixture.

A subject of the present invention is also a strain of *Saccharomyces* derived from the strain CNCM I-3886, the strain CNCM I-3887, the strain CNCM I-3888, the strain CNCM I-4132, the strain CNCM I-4133, the strain CNCM I-4129, of the strain CNCM I-4130 or the strain CNCM I-4131, characterized in that in the presence of a culture medium comprising a mixture of glycerol and sugar, it consumes at least 80% of the glycerol in said mixture, said mixture comprising a proportion of glycerol of at least 20% as saccharose equivalent, the sum of the proportions of glycerol and sugar in said mixture being equal to 100% as saccharose equivalent.

A subject of the present invention is also a strain of *Saccharomyces* derived from the strain CNCM I-3886, the strain CNCM I-3887, the strain CNCM I-3888, the strain CNCM I-4132, the strain CNCM I-4133, the strain CNCM I-4129, the strain CNCM I-4130 or the strain CNCM I-4131, characterized in that in the presence of a culture medium comprising a mixture of glycerol and sugar, it consumes at least 80% of the glycerol in said mixture, said mixture comprising a proportion of glycerol of 20% as saccharose equivalent, the sum of the proportions of glycerol and sugar in said mixture being equal to 100% as saccharose equivalent.

By the expression "derived strain", is meant a strain derived by any conversion whatever, such as for example by one or more crossings and/or by mutation and/or by genetic transformation.

A subject of the present invention is also the use of a strain of yeast as defined above, for the production of yeasts, in the presence of a mixture of glycerol and sugar, said mixture comprising a proportion of glycerol of at least 5% as saccharose equivalent, the sum of the proportions of glycerol and sugar in said mixture being equal to 100% as saccharose equivalent.

A subject of the present invention is the use of a strain of yeast as defined above, for the industrial production of yeasts, in the presence of a mixture of glycerol and sugar.

A subject of the present invention is the use of a strain of yeast as defined above, for the production of yeasts, the production being carried out according to a standard system well known to a person skilled in the art, but carried out under aerobic conditions and using a mixture of glycerol and sugar as a source of carbon.

A subject of the present invention is also the use of a mixture of glycerol and sugar for the production of yeasts from at least one strain of *Saccharomyces*, characterized in that said strain consumes at least 80% of the glycerol in said mixture, said mixture comprising a proportion of glycerol of at least 5% as saccharose equivalent, the sum of the proportions of glycerol and sugar in said mixture being equal to 100% as saccharose equivalent.

Such a use is of particular interest for the production of yeasts on an industrial scale.

The expression at least one strain of *Saccharomyces* means that the production of yeasts can be carried out from several different strains of yeasts, of the same species or of different species.

Preferably, the production of yeasts is carried out from a single strain of yeast.

The mixture of glycerol and sugar is as defined above.

A subject of the present invention is the use of a mixture of glycerol and sugar for the production of yeasts as defined above, characterized in that the production of yeasts is carried out according to a semi-continuous or continuous mode.

A subject of the present invention is the use of a mixture of glycerol and sugar for the production of yeasts as defined above, characterized in that the production of yeasts is carried out under aerobic conditions.

A subject of the present invention is the use of a mixture of glycerol and sugar for the production of yeasts as defined above, characterized in that the production of yeasts is carried out over a period preferably less than 48 hours, more preferentially less than 36 hours, even more preferentially less than 24 hours.

Advantageously, the production period is comprised between 10 hours and 24 hours.

The production period is for example 22 hours.

A subject of the present invention is the use of a mixture of glycerol and sugar for the production of yeasts as defined above, characterized in that the production yield is similar to that obtained with a standard strain of yeast produced in the absence of glycerol.

For example, the production yield of yeasts according to the invention is greater than 85%, preferably greater than 90%, more preferentially greater than 95% of the yield of a standard strain produced in the absence of glycerol.

By standard strain, is meant for example the baker's yeast deposited at the NCYC under number NCYC 995.

By "yield" or "production yield" or "biomass production yield", is meant the ratio of the mass of yeast produced to the mass of saccharose equivalent utilized.

The mass of saccharose equivalent utilized is constituted by the mass of saccharose equivalent consumed and that not consumed.

The culture medium is as defined above.

According to another embodiment, a subject of the present invention is the use of a mixture of glycerol and sugar for the production of yeasts as defined above, characterized in that the culture medium comprises another source of carbon which can be assimilated by the strain of yeast. Another source of carbon which can be assimilated by the strain of yeast is for example ethanol. In such an embodiment the mixture of glycerol and sugar constitutes at least 70% of the carbon source for the yeast, preferably at least 80% of the carbon source for the yeast, more preferentially at least 90% of the carbon source for the yeast.

A subject of the present invention is the use of a mixture of glycerol and sugar for the production of yeasts as defined above, characterized in that not all of the culture medium is placed in the presence of the strain of yeast as from the start of the culture.

The culture medium is preferably placed in the presence of the strain of yeast of in manner spread over time, at a constant or variable rate, the different constituents of the culture medium which can be supplied at the same time or separately.

A subject of the present invention is the use of a mixture of glycerol and sugar for the production of yeasts as defined above, characterized in that the mixture of glycerol and sugar is introduced into the culture medium in a manner spread over time.

A subject of the present invention is the use of a mixture of glycerol and sugar for the production of yeasts as defined above, characterized in that the mixture of glycerol and sugar is introduced into the culture medium separately from the other constituents of the culture medium.

A subject of the present invention is the use of a mixture of glycerol and sugar for the production of yeasts as defined above, characterized in that the mixture of glycerol and sugar is prepared before its introduction into the culture medium and/or is formed in the culture medium, when the glycerol and the sugar are supplied separately.

A subject of the present invention is the use of a mixture of glycerol and sugar for the production of yeasts as defined above, characterized in that the strain is not placed in culture in the presence of all of the glycerol and/or of all of the sugar in the mixture as from the start of the culture.

A particular subject of the present invention is the use as defined above of a mixture of glycerol and sugar for the production of yeasts from at least one strain of *Saccharomyces*, characterized in that said strain consumes at least 85% of the glycerol in the mixture, preferably at least 90% of the glycerol in the mixture, more preferentially at least 95% of the glycerol in the mixture, even more preferentially at least 98% of the glycerol in the mixture.

A subject of the present invention is also the use as defined above of a mixture of glycerol and sugar for the production of yeasts, characterized in that said mixture comprises a proportion of glycerol of at least 8% as saccharose equivalent, preferably at least 10% as saccharose equivalent, more preferentially at least 12% as saccharose equivalent, even more preferentially at least 15% as saccharose equivalent, even more preferentially at least 17% as saccharose equivalent, even more preferentially at least 20% as saccharose equivalent.

A particular subject of the present invention is the use as defined above of a mixture of glycerol and sugar for the production of yeasts, characterized in that the proportion of glycerol in said mixture comprises 8% to 30% as saccharose equivalent, preferably 10% to 20% as saccharose equivalent, more preferentially 12% to 17% as saccharose equivalent.

A subject of the present invention is also the use as defined above of a mixture of glycerol and sugar for the production of yeasts, characterized in that said mixture comprises a proportion of glycerol of at least 30% as saccharose equivalent, preferably at least 40% as saccharose equivalent, more preferentially at least 50% as saccharose equivalent, even more preferentially at least 60% as saccharose equivalent, even more preferentially at least 70% as saccharose equivalent, even more preferentially at least 80% as saccharose equivalent, even more preferentially at least 90% as saccharose equivalent.

A subject of the present invention is also the use as defined above of a mixture of glycerol and sugar for the production of yeasts, characterized in that the proportion of glycerol in said mixture is at most 95% as saccharose equivalent, preferably at most 90% as saccharose equivalent, more preferentially at most 85% as saccharose equivalent.

A particular subject of the present invention is the use as defined above of a mixture of glycerol and sugar for the production of yeasts, characterized in that the proportion of glycerol in said mixture comprises 30% to 90% as saccharose equivalent, preferably 40% to 80% as saccharose equivalent, more preferentially 50% to 70% as saccharose equivalent.

A subject of the present invention is the use as defined above of a mixture of glycerol and sugar for the production of yeasts from a strain, characterized in that said strain is chosen from the species *cerevisiae, boulardii, carlsbergensis* and *uvarum*.

A subject of the present invention is the use as defined above of a mixture of glycerol and sugar for the production of yeasts from at least one strain of *Saccharomyces*, characterized in that said strain is chosen from a natural variant and/or a genetically modified strain.

A subject of the present invention is the use as defined above of a mixture of glycerol and sugar for the production of yeasts from at least one strain of *Saccharomyces*, characterized in that said strain is chosen from
- the strain deposited with the CNCM on 20 Dec. 2007 under number CNCM I-3886,
- the strain deposited with the CNCM on 20 Dec. 2007 under number CNCM I-3887,
- the strain deposited with the CNCM on 20 Dec. 2007 under number CNCM I-3888,
- the strain deposited with the CNCM on 3 Mar. 2009 under number I-4132,
- the strain deposited with the CNCM on 3 Mar. 2009 under number I-4133,
- the strain deposited with the CNCM on 3 Mar. 2009 under number I-4129,
- the strain deposited with the CNCM on 3 Mar. 2009 under number I-4130 or
- the strain deposited with the CNCM on 3 Mar. 2009 under number I-4131, or a mixture thereof.

A subject of the present invention is also the yeasts obtained by the use as defined above of a mixture of glycerol and sugar.

A subject of the present invention is also a method for the production of yeasts comprising the stages of:

introduction of a strain of yeast of the genus *Saccharomyces* into a fermenter, and multiplication of said strain under aerobic conditions in a culture medium comprising a mixture of glycerol and sugar, said mixture comprising a proportion of glycerol of at least 5% as saccharose equivalent, the sum of the proportions of glycerol and sugar in said mixture being equal to 100% as saccharose equivalent.

The mixture of glycerol and sugar is as defined above.

The culture medium is as defined above.

A subject of the present invention is a method for the production of yeasts as defined above, characterized in that the multiplication of said strain is carried out according to a semi-continuous mode or according to a continuous mode, the semi-continuous or continuous modes being as defined above.

The duration of culture of the method for the production of yeasts according to the invention is preferably less than 48 hours, more preferentially less than 36 h, even more preferentially less than 24 hours.

Advantageously, the duration of the culture of the method for the production of yeasts according to the invention is comprised between 10 hours and 24 hours.

The production period is for example 22 hours.

The pH is adjusted preferably to a value comprised between 4 and 6.5, for example by simultaneous supply of acids or bases.

The temperature is adjusted preferably to a value comprised between 30° C. and 34° C., for example by heating or cooling down of the fermenter.

Advantageously, the method for the production of yeasts according to the invention produces yields similar to those obtained with standard strains of yeast produced in the absence of glycerol.

For example, the production yield of yeasts according to the invention is greater than 85%, preferably greater than 90%, more preferentially greater than 95% of the yield of a standard strain produced in the absence of glycerol.

By standard strain, there can for example be mentioned the baker's yeast deposited at the NCYC under number NCYC 995.

By "yield", is meant the ratio of the mass of yeast produced to the mass of saccharose equivalent utilized.

The mass of saccharose equivalent utilized is constituted by the mass of saccharose equivalent consumed and that not consumed.

The yeasts obtained by culture of strains according to the invention in the presence of a mixture of glycerol and sugar and/or the yeasts obtained according to the method for the production of yeast of the invention have similar qualities to the yeasts used in a standard fashion and produced on a carbonaceous substrate of sugar type (in the absence of glycerol).

By the term "quality", is meant both the functional quality and the preservation qualities.

For example, said yeasts have similar qualities in terms of resistance to drying, in terms of production yield, in terms of fermenting power for breadmaking yeasts, in terms of production of alcohol and/or resistance to strong concentrations of alcohol for the alcohol yeasts to the yeasts used in a standard fashion and produced on a carbonaceous substrate of sugar type (in the absence of glycerol).

The yeasts obtained by culture of strains according to the invention in the presence of a mixture of glycerol and sugar and/or the yeasts obtained according to the method for the production of yeast of the invention have an intracellular glycerol concentration preferably less than 1.5% by mass of dry matter, more preferentially less than 1%.

This low concentration of intracellular glycerol reflects the absence of accumulation of glycerol in the medium and therefore the fact that it has been metabolized.

In a particular embodiment, the culture medium comprises another source of carbon which can be assimilated by the strain of yeast. Another source of carbon which can be assimilated by the strain of yeast is for example ethanol. In such an embodiment, the mixture of glycerol and sugar constitutes at least 70% of the carbon source for the yeast, preferably at least 80% of the carbon source for the yeast, more preferentially at least 90% of the carbon source for the yeast.

In a preferred embodiment, not all of the culture medium is placed in the presence of the strain of yeast as from the start of the culture. The culture medium is preferably placed in the presence of the strain of yeast in a manner spread over time, at a constant or variable rate, the different constituents of the culture medium being able to be supplied at the same time or separately.

In a preferred embodiment according to the invention, the mixture of glycerol and sugar is introduced into the culture medium in a manner spread over time.

In a preferred embodiment according to the invention, the mixture of glycerol and sugar is introduced into the culture medium separately from the other constituents of the culture medium.

The mixture of glycerol and sugar can be prepared before its introduction into the culture medium and/or be formed in the culture medium, when the glycerol and the sugar are supplied separately.

In a preferred embodiment according to the invention, the strain is not placed in culture in the presence of all of the glycerol and/or all of the sugar in the mixture as from the start of the culture.

A subject of the present invention is also a method for the production of yeast as defined above comprising the stages of:

introduction of a strain of yeast of the genus *Saccharomyces* into a fermenter, optionally multiplication of said strain under aerobic conditions in a culture medium comprising no glycerol, multiplication of said strain under aerobic conditions, according to a semi-continuous or continuous mode, in a culture medium comprising a mixture of glycerol and sugar, said mixture comprising a proportion of glycerol of at least 5% as saccharose equivalent, the sum of the proportions of glycerol and sugar in said mixture being equal to 100% as saccharose equivalent, optionally multiplication of said strain under aerobic conditions in a culture medium comprising no glycerol.

A subject of the present invention is a method for the production of yeasts comprising the stages of introduction of a strain of yeast of the genus *Saccharomyces* into a fermenter, optionally multiplication of said strain under aerobic conditions in a culture medium comprising no glycerol, multiplication of said strain under aerobic conditions in a culture medium comprising a mixture of glycerol and sugar, said mixture comprising a proportion of glycerol of at least 5% as saccharose equivalent, the sum of the proportions of glycerol and sugar in said mixture being equal to 100% as saccharose equivalent, optionally, multiplication of said strain under aerobic conditions in a culture medium comprising no glycerol, and separation by centrifugation of the baker's yeast thus produced from its culture medium, obtaining a liquid "yeast cream" containing approximately between 14 and 25% of dry matter, or even higher dry matter if the yeast cream is mixed with osmotic products.

A subject of the present invention is also the method for the production of yeasts as defined above comprising optional subsequent stages of:
- filtration of the liquid yeast cream thus obtained, in general on a rotary filter under vacuum, obtaining a dehydrated fresh yeast containing approximately 26 to 35% dry matter,
- mixing of said dehydrated fresh yeast in order to obtain of a very homogenous mass,
- extrusion of the yeast thus obtained, obtaining a yeast pressed into the shapes of loaves of fresh yeast or of crumbled fresh yeast, marketed with approximately 30% dry matter, or if the yeast is intended to be dried, in the form of vermicelli,
- drying in controlled manner, in a current of warm air, for example by fluidization, of the particles of yeasts obtained by extrusion, and
- packaging.

A particular subject of the present invention is a method for the production of yeasts as defined above, characterized in that at least 80% of the glycerol in said mixture is consumed by said strain, preferably at least 85% of the glycerol in said mixture, more preferentially at least 90% of the glycerol in said mixture, even more preferentially at least 95% of the glycerol in said mixture, even more preferentially at least 98% of the glycerol in said mixture.

A subject of the present invention is also a method for the production of yeasts as defined above, characterized in that said mixture comprises a proportion of glycerol of at least 8% as saccharose equivalent, preferably at least 10% as saccharose equivalent, more preferentially at least 12% as saccharose equivalent, even more preferentially at least 15% as saccharose equivalent, even more preferentially at least 17% as saccharose equivalent, even more preferentially at least 20% as saccharose equivalent.

A particular subject of the present invention is a method for the production of yeasts as defined above, characterized in that the proportion of glycerol in said mixture comprises 8% to 30% as saccharose equivalent, preferably 10% to 20% as saccharose equivalent, more preferentially 12% to 17% as saccharose equivalent.

A particular subject of the present invention is a method for the production of yeasts as defined above, characterized in that said mixture comprises a proportion of glycerol of at least 30% as saccharose equivalent.

A more particular subject of the present invention is a method for the production of yeasts as defined above, characterized in that said mixture comprises a proportion of glycerol of at least 40% as saccharose equivalent, preferably at least 50% as saccharose equivalent, more preferentially at least 60% as saccharose equivalent, even more preferentially at least 70% as saccharose equivalent, even more preferentially at least 80% as saccharose equivalent, even more preferentially at least 90% as saccharose equivalent.

A subject of the present invention is also a method for the production of yeasts as defined above, characterized in that the proportion of glycerol in said mixture is at most 95% as saccharose equivalent, preferably at most 90% as saccharose equivalent, more preferentially at most 85% as saccharose equivalent.

A particular subject of the present invention is a method for the production of yeasts as defined above, characterized in that the proportion of glycerol in said mixture comprises 30% to 90% as saccharose equivalent, preferably 40% to 80% as saccharose equivalent, more preferentially 50% to 70% as saccharose equivalent.

A subject of the present invention is a method for the production of yeasts as defined above, characterized in that said strain of yeast is chosen from the species *cerevisiae, boulardii, carlsbergensis* and *uvarum*.

A subject of the present invention is a method for the production of yeasts as defined above, characterized in that said strain of yeast is chosen from a natural variant and/or a genetically modified strain.

A subject of the present invention is a method for the production of yeasts as defined above, characterized in that said strain of yeast is chosen from
- the strain deposited with the CNCM on 20 Dec. 2007 under number CNCM I-3886,
- the strain deposited with the CNCM on 20 Dec. 2007 under number CNCM I-3887,
- the strain deposited with the CNCM on 20 Dec. 2007 under number CNCM I-3888,
- the strain deposited with the CNCM on 3 Mar. 2009 under number I-4132,
- the strain deposited with the CNCM on 3 Mar. 2009 under number I-4133,
- the strain deposited with the CNCM on 3 Mar. 2009 under number I-4129,
- the strain deposited with the CNCM on 3 Mar. 2009 under number I-4130 or
- the strain deposited with the CNCM on 3 Mar. 2009 under number I-4131, or a mixture thereof.

A subject of the present invention is a method as defined above, characterized in that said strain of yeast is a strain as defined above.

A subject of the present invention is also yeasts which can be obtained by the implementation of the method for the production of yeasts as defined above.

In a particular embodiment of the invention, the residual glycerol is recycled in order to be used in a mixture of glycerol and sugar.

According to another embodiment, the mixture constituted by glycerol and sugar can comprise a proportion of glycerol ranging up to 99.9% as saccharose equivalent, or even virtually 100% as saccharose equivalent.

The following examples illustrate the invention without limiting it.

EXAMPLES

Example 1

Obtaining Genetically Modified Strains of Yeast According to the Invention

Material and Methods

The STL1 (YDR536w) gene encodes the active glycerol permease. This gene was amplified from the genomic DNA of an industrial yeast and sequenced.

The sequence of the amplified STL1 gene, composed of 1710 nucleotides, was aligned with the nucleotide sequence of the ORF YDR536w originating from the S288c yeast (SGD database). The alignment demonstrated the presence of 7 different nucleotides over the whole sequence, which corresponds to an identity percentage of 99.6%.

The translation of the nucleotide sequence of the STL1 gene originating from the industrial yeast, leads to a protein of 570 amino acids. The alignment of the protein sequence of the STL1 gene originating from the industrial yeast with the protein sequence of the ORF YDR536w originating from the S288c yeast demonstrated the presence of 3 different amino acids, which corresponds to an identity percentage of 99.5%.

The construction of genetically modified industrial strains of yeast is based on a molecular tool suited to the industrial yeasts constructed by the Applicant.

This tool allows in particular:
the cloning of a gene of interest, here the STL1 gene, between the ADH1 promoter and the CYC1 terminator of yeast, which allows the expression of this gene in the yeast—
the presence on either side of the expression cassette of 2 recombinogenic fragments (BUD5-A and BUD5-B, each of 500 nucleotides), which allows the insertion by homologous recombination of the cassette into the yeast genome, after transformation, at the BUD5 locus (YCR038c) located on the chromosome III,
the presence of the KANMX selection marker, framed by 2 loxP sites, which allows the selection of clones of yeasts having integrated the expression cassette containing the STL1 gene into their genome; these same clones are then transformed with a plasmid bearing the Cre gene encoding for a recombinase placed under the control of the Gal1 promoter; after induction of the expression of this gene by culture in medium containing galactose, the action of the recombinase will induce the loss of the DNA fragment containing the KANMX selection marker.

The expression cassette is shown in FIG. 1.
The 5 starting strains used are the following:
the strain of *Saccharomyces cerevisiae* deposited at the CNCM under number I-3399,
the strain of *Saccharomyces cerevisiae* deposited at the NCYC under number NCYC996,
the strain of *Saccharomyces cerevisiae* deposited at the NCYC under number NCYC995,
the strain of *Saccharomyces cerevisiae* deposited at the CNCM under number I-4072, and
the strain of *Saccharomyces cerevisiae* deposited at the CNCM under number I-4071.

Each of the starting strains is transformed with the expression cassette. The geneticin-resistant clones are selected. Then, for each clone selected, the integration of the expression cassette into the yeast genome at the correct locus is verified by PCR. The clones selected are then transformed with a plasmid bearing the Cre gene encoding for a recombinase placed under the control of the Gal1 promoter. After induction of the expression of this Cre gene by culture in galactose-containing medium, the action of the recombinase makes it possible to induce the loss of the DNA fragment containing the KANMX selection marker. The loss of said KANMX selection marker at the site of integration into the chromosome is then verified by PCR, the presence of the expression cassette containing the STL1 gene in the yeast genome at the correct locus by PCR, as well as the loss of the resistance to geneticin. The loss of the Cre plasmid is verified by the loss of resistance to nourseothricin.

Finally, the transcription of the STL1 gene in the presence of sugar into the genetically modified strain is verified by measuring the level of mRNA originating from the transcription of the STL1 gene placed under the control of the ADH1 promoter. To this end, the modified strain is cultured in the presence of sugar (YPG laboratory culture medium containing 2% glucose). The mRNA is extracted from said strains and the mRNA level corresponding to the transcription of the STL1 gene is measured by quantitative PCR. The mRNA level of the mutated strain is then expressed as a function of the mRNA level of the corresponding non-mutated strain (fixed at 1).

Results

The strains genetically modified for expressing the STL1 gene thus obtained were deposited at the CNCM under the following numbers:
strain number I-3886, originating from the starting strain deposited at the CNCM under number I-3399,
strain number I-3887, originating from the starting strain deposited at the NCYC under number NCYC 996,
strain number I-3888, originating from the starting strain of *Saccharomyces cerevisiae* deposited at the NCYC under number NCYC995,
strain number I-4132, originating from the starting strain deposited at the CNCM under number I-4072, and
strain number I-4133, originating from the starting strain deposited at the CNCM under number I-4071.

The transcription rates indicated in FIG. 2 show a large increase (from 270 to 300 times) in the transcription of the STL1 gene in the three genetically modified strains I-3886, I-3887 and I-3888 cultured in the presence of sugar, in comparison with the transcription rate of the gene in the corresponding non-mutated control strain cultured in the same medium.

As regards the transcription rate of strains I-4132 and I-4133 cultured in the presence of sugar, a large increase (greater than 200 times) in the transcription of the STL1 gene is also demonstrated, in comparison with the transcription rate of the gene in the corresponding non-mutated control strain cultured in the same medium.

Example 2

Production of Yeasts from Genetically Modified Strains According to the Invention on a Mixture of Glycerol and Sugar Material and Methods
(i) Semi-Continuous Mode The production of fresh yeast is carried out in the manner described in the work "Yeast technology", 2nd edition, 1991, G. Reed and T. W. Nagodawithana, published by Van Nostrand Reinhold, ISBN 0-442-31892-8.

The fermenter used is seeded with a certain initial volume containing water, a little nitrogen and phosphorus, nutritive elements such as vitamins and minerals.

Before seeding the fermenter with a certain quantity of live yeast strains, a little molasses is added in order to start the culture. The pH and the temperature are adjusted to values comprises respectively between 3.5 and 7 for the pH (with simultaneous supplies of acid or base as needed), and between 30 and 34° C. for the temperature (with heating or cooling of the fermenter as needed). The so-called "fed-batch" culture in semi-continuous mode is started by supplying molasses or a mixture of molasses and glycerol comprising a proportion of glycerol of 20% as saccharose equivalent. The flow rate of the molasses or the mixture of glycerol and molasses determines the growth rate of the yeasts. This variable flow rate is fixed over time so that the saccharose equivalent supplied over time can be completely respired (oxidized) by the yeast. Under such conditions, the production of ethanol by the yeast over time is zero, or limited to the first hours of the test. In order to meet these conditions, the culture is for example carried out at an average growth rate of 0.16 h−1 for the strains I-3886, I-3887, I-3888 and the corresponding non-GMO strains, and at an average growth rate of 0.13 h−1 for the strains I-4132 and I-4133 and the corresponding non-GMO strains.

The medium is sufficiently aerated and mixed so as not to be limiting in terms of oxygen.

In addition to the molasses or the mixture of glycerol and molasses, a continuous source of nitrogen in the form of urea and phosphorus in the form of phosphoric acid makes it possible to respond to the needs of the yeast for the synthesis of the proteins and other cell constituents.

The supply of molasses or the mixture of glycerol and molasses is maintained for 22 hours so as to obtain the desired quantity of yeast, taking account of the equipment utilized.

During the last hours of culture, the supply of molasses or the mixture of glycerol and molasses is progressively reduced so as to reduce the level of budding yeasts in the fermenter.

According to this method of use, the carbon substrate feed (for example the mixture of glycerol and molasses comprising a proportion of glycerol of 20% as sugar equivalent) makes it possible to multiply the initial biomass by 40 in 22 hours of culture, while maintaining a metabolism which is mostly respiratory and guaranteeing a budding rate when harvested less than 5-10%. The total quantity of poured carbonaceous substrate is a function of the oxygen transfer capacity and calories in the fermentation tank.

The final biomass concentration is comprised between 5 and 7% and the nitrogen content of this biomass between 6 and 9%.

During the culture and at the end of culture, the quantity of glycerol in the culture medium is measured by HPLC and is compared to the quantity of glycerol supplied.

At the end of the culture, the yeast is harvested by centrifugation and the mass of yeast harvested is measured.

The yeast produced (in g of DM) is the difference between the yeast harvested (in g of DM) and the yeast in the inoculum (in g of DM) (DM meaning Dry Matter).

The percentage yield is then obtained by taking the ratio of "yeast produced (g of DM)"/"carbonaceous substrate introduced as saccharose equivalent (g)" and multiplying by 100.

The percentage of glycerol consumed is calculated by taking the ratio $$\frac{\text{"quantity of glycerol measured at the end of culture }(g)\text{"}}{\text{"quantity of glycerol supplied during the culture }(g)\text{"}}$$

and multiplying by 100.
(ii) Chemostat Mode

The fermenter is fed by a source of carbon constituted by a mixture of glycerol and sugar, a source of nitrogen, a source of sulphur and a source of phosphorus. Vitamins and minerals are supplied in excess.

Mixtures of glycerol and glucose comprising 0% to 80% glycerol as saccharose equivalent are tested.

The fermenter is placed on a balance which controls a draw-off pump in order to keep the volume in the fermenter constant by controlling its weight. The culture is limited by the carbonaceous substrate (glucose and glycerol), the other constituents being supplied in excess. The medium is sufficiently aerated and mixed so as never to be limiting in terms of oxygen.

The medium is supplied continuously at a constant flow rate making it possible to obtain a dilution rate (=flow rate/volume) of 0.15 h$^{-1}$ and therefore in steady state a constant growth rate of 0.15 h$^{-1}$.

The concentration of saccharose equivalent in the feed medium is equal to 19 g/kg.

The yield as well as the residual quantity of glycerol are measured in the culture in steady state.

The steady state is reached when the concentrations in the fermenter are stable for at least 3 residence times, the residence time being the ratio 1/[dilution rate].

The biomass production yield on supplied sugar is the ratio of the biomass produced to the supplied sugar. In steady state, the biomass produced per unit of time is equal to the draw-off rate multiplied by the concentration of biomass in the fermenter (determined by filtering a known volume of yeast-containing wort and weighing the cake of yeast which has been previously washed and dried).

At the time of the determination of the yield a sample of yeast-containing wort is taken and immediately filtered in order to remove the biomass. The filtrate is analyzed by HPLC in order to assay the residual quantity of glycerol.
Results
(i) Semi-Continuous Mode The non-mutated strains I-3399, NCYC 996, NCYC 995, I-4072 and I-4071 and the corresponding mutated strains, I-3886, I-3887, I-3888, I-4132 and I-4133 respectively, were produced according to the procedure described above, with, as a source of carbon, pure molasses or a mixture of glycerol and molasses comprising a proportion of glycerol of 20% as saccharose equivalent.

Figure 3:
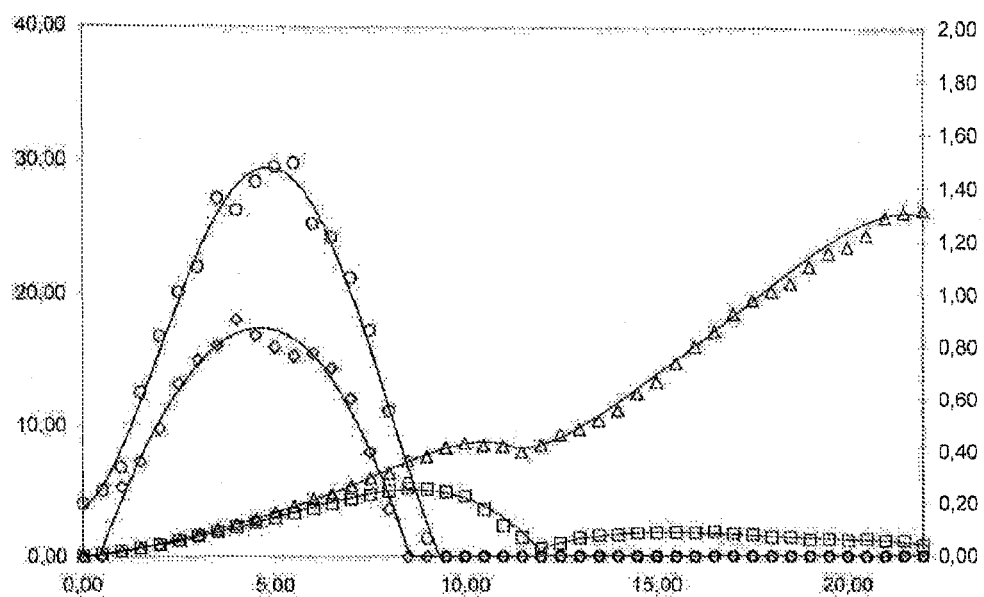
FIG. 3: Residual quantity of glycerol, after culture in semi-continuous mode, of the strain I-3887 in comparison to that of the non-mutated strain NCYC 996, as a function of time.
The mixture comprised 20% glycerol as saccharose equivalent. The y-axis on the left indicates the quantity of glycerol (in g) and the y-axis on the right the quantity of ethanol (in g) in the medium free from yeasts. The x-axis indicates the time (in hours). The curve with triangles represents the residual quantity of glycerol in the medium free from yeasts during culture of the non-mutated strain NCYC 996 and the curve with squares that of the strain I-3887. The curve with circles represents the residual quantity of ethanol in the medium free from yeasts during culture of the non-mutated strain NCYC 996 and the curve with diamonds that of the strain I-3887.
Figure 4:
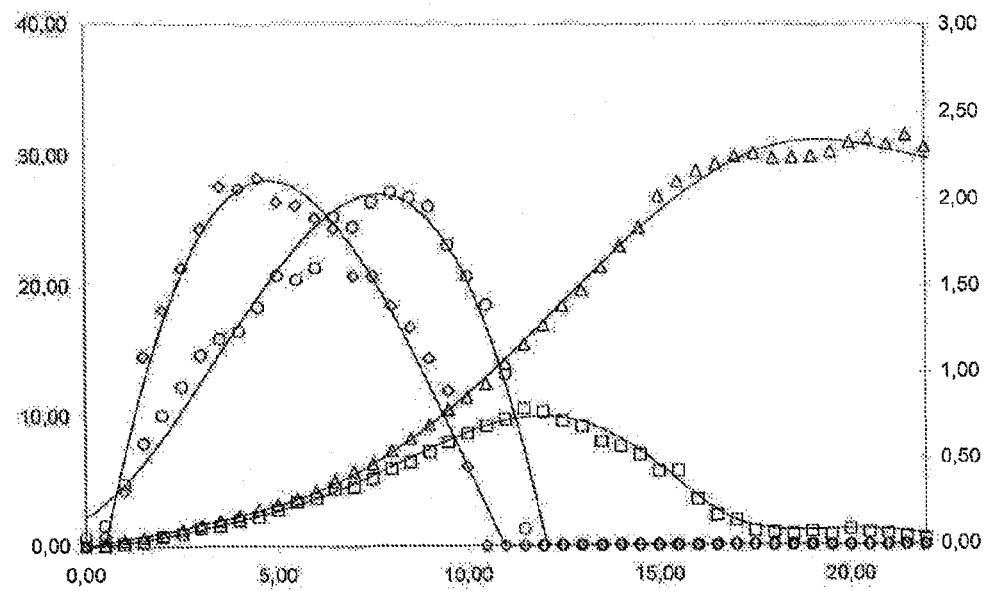
FIG. 4: Residual quantity of glycerol, after culture in semi-continuous mode, of the strain I-3888 in comparison to that of the non-mutated strain NCYC 995, as a function of time.
The mixture comprised 20% glycerol as saccharose equivalent. The y-axis on the left indicates the quantity of glycerol (in g) and the y-axis on the right the quantity of ethanol (in g) in the medium free from yeasts. The x-axis indicates the time (in hours). The curve with triangles represents the residual quantity of glycerol in the medium free from yeasts during culture of the non-mutated strain NCYC 995 and the curve with squares that of the strain I-3888. The curve with circles represents the residual quantity of ethanol in the medium free from yeasts during culture of the non-mutated strain NCYC 995 and the curve with diamonds that of the strain I-3888.

FIGS. 3 and 4 and Tables 1, 2, 3, 4 and 5 illustrate the results obtained with the non-mutated strains and the corresponding mutated strains.

The production yield is determined for each non-mutated strain in the presence of pure molasses (without glycerol). In Tables 1, 2, 3, 4 and 5, the values indicated on the line "yield" correspond to the percentage yield with respect to the yield of the non-mutated strain produced on pure molasses.

Table 1 indicates the results of the tests carried out with the non-mutated strain NCYC 996 and the corresponding mutated strain I-3887.

Table 2 indicates the results of the tests carried out with the non-mutated strain I-3399 and the corresponding mutated strain I-3886.

Table 3 indicates the results of the tests carried out with the non-mutated strain NCYC 995 and the corresponding mutated strain I-3888.

Table 4 indicates the results of the tests carried out with the non-mutated strain I-4072 and the corresponding mutated strain I-4132.

Table 5 indicates the results of the tests carried out with the non-mutated strain I-4071 and the corresponding mutated strain I-4133.

On reading these tables, it is noted that during a production on a mixture of glycerol and molasses (comprising a proportion of glycerol of 20% as saccharose equivalent) as source of carbon, the production yield obtained with the non-mutated strains is significantly less than the production yield obtained on pure molasses. This reduction in the yield is to be linked to the non-use of a significant part of the saccharose equivalent supplied in the form of glycerol, the glycerol accumulating in the culture medium as indicated in the results on the line "supplied glycerol consumed".

These same tables show the results of the tests carried out with the mutated strains, when the source of carbon supplied is a mixture of molasses and glycerol. The measurements carried out indicate that the consumption of the glycerol supplied is practically total for the three mutated strains I-3887, I-3886 and I-3888 (consumption of glycerol greater than 99%), which results in production yields at least equivalent to those obtained with non-mutated strains produced on pure molasses (Tables 1 to 3).

As regards the mutated strains I-4132 and I-4133, the consumption of the glycerol supplied is greater than 80% and the yield is greater than 90% of the yield obtained with the non-GMO strain in the absence of glycerol (Tables 4 and 5).

This difference in consumption of the glycerol by the non-mutated strains and the corresponding mutated strains is illustrated in FIGS. 3 and 4 which show the accumulation of glycerol over time, during production tests on a mixture of glycerol and molasses comprising a proportion of 20% of glycerol as saccharose equivalent.

The curve with triangles in FIG. 3 represents the residual quantity of glycerol in the medium free from yeasts during culture of the non-mutated strain NCYC 996 and the curve with squares that of the strain I-3887.

The curve with triangles in FIG. 4 represents the residual quantity of glycerol in the medium free from yeasts during culture of the non-mutated strain NCYC 996 and the curve with squares that of the mutated strain I-3888.

The difference in consumption between the non-mutated strains and the corresponding mutated strains is significant after the five first hours of culture. During the first five hours of culture, the respiratory capacity of the non-mutated strains and the mutated strains is saturated by the sugar supplied ("Crabtree" effect), this phenomenon being accompanied by production of ethanol. When this phenomenon disappears, i.e. when the yeasts have the respiratory capacity to oxidize all of the sugar and glycerol supplied, the mutated strains consume virtually all of the glycerol supplied simultaneously with the sugar, whereas the non-mutated strains accumulate the glycerol.

TABLE 1

|  | 0% glycerol | 20% glycerol | |
| --- | --- | --- | --- |
|  | NCYC 996 | NCYC 996 | I-3887 |
| Yield (as a percentage of the yield of the control strain in the absence of glycerol) | 100.0 | 89.6 | 102.5 |
| Supplied glycerol consumed (in %) | / | 65.5 | 99.2 |

TABLE 2

|  | 0% glycerol | 20% glycerol | |
| --- | --- | --- | --- |
|  | I-3399 | I-3399 | I-3886 |
| Yield (as a percentage of the yield of the control strain in the absence of glycerol) | 100.0 | 93.8 | 108.1 |
| Supplied glycerol consumed (in %) | / | 48.9 | 99.1 |

TABLE 3

|  | 0% glycerol | 20% glycerol | |
| --- | --- | --- | --- |
|  | NCYC 995 | NCYC 995 | I-3888 |
| Yield (as a percentage of the yield of the control strain in the absence of glycerol) | 100.0 | 93.7 | 100.9 |
| Supplied glycerol consumed (in %) | / | 57.9 | 98.9 |

TABLE 4

|  | 0% glycerol | 20% glycerol | |
| --- | --- | --- | --- |
|  | I-4072 | I-4072 | I-4132 |
| Yield (as a percentage of the yield of the control strain in the absence of glycerol) | 100.0 | 78.7 | 93.3 |
| Supplied glycerol consumed (in %) | / | 22.7 | 83.9 |

TABLE 5

|  | 0% glycerol | 20% glycerol | |
| --- | --- | --- | --- |
|  | I-4071 | I-4071 | I-4133 |
| Yield (as a percentage of the yield of the control strain in the absence of glycerol) | 100.0 | 88.2 | 92.9 |
| Supplied glycerol consumed (in %) | / | 44.8 | 84.2 |

(ii) Continuous Mode

Figure 5:
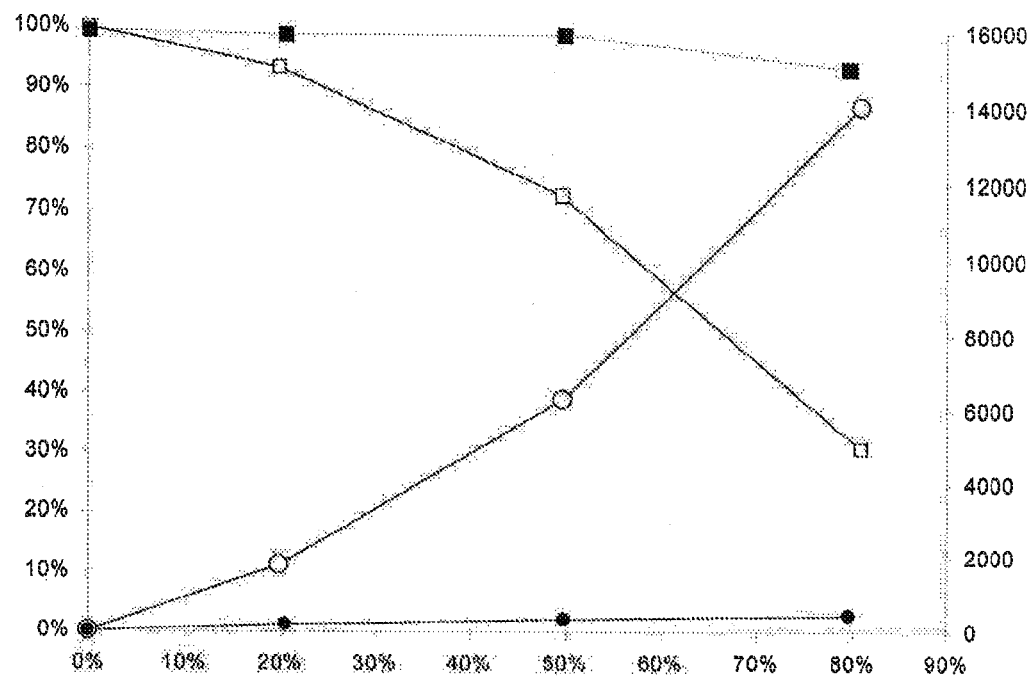
FIG. 5: Yield and residual concentration of glycerol after culture in chemostat mode of the strain I-3887 and of the strain NCYC 996, as a function of the proportion of glycerol in the mixture of glycerol and sugar in the feed medium. The y-axis on the left indicates the yield of the strain as a percentage with respect to the yield of the strain NCYC 996 cultured in the absence of glycerol. The y-axis on the right indicates the residual concentration of glycerol in the medium free from yeasts (in ppm). The x-axis indicates the proportion of glycerol in the mixture of glycerol and sugar as saccharose equivalent. The production yield is represented by squares and the residual concentration of glycerol by circles. The results of the non-mutated strain NCYC 996 (control) are shown in white and those of the corresponding mutated strain I-3887 in black.
Figure 6:
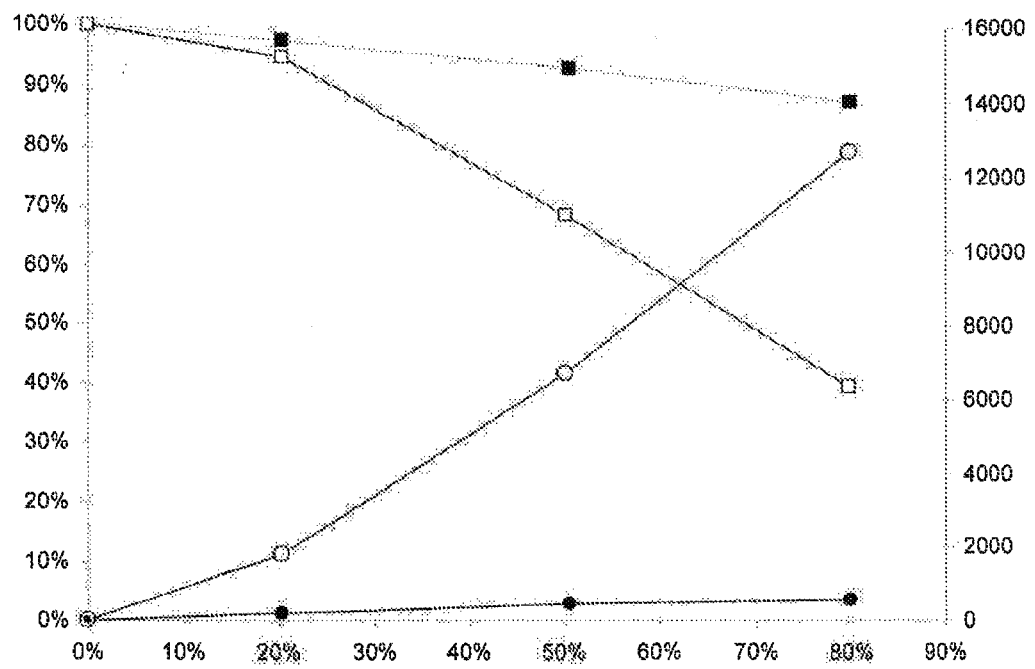
FIG. 6: Yield and residual concentration of glycerol after culture in chemostat mode of the strain I-3888 and of the strain NCYC 995, as a function of the proportion of glycerol in the mixture of glycerol and sugar in the feed medium. The y-axis on the left indicates the yield of the strain as a percentage with respect to the yield of the strain NCYC 995 cultured in the absence of glycerol. The y-axis on the right indicates the residual concentration of glycerol in the medium free from yeasts (in ppm). The x-axis indicates the proportion of glycerol in the mixture of glycerol and sugar as saccharose equivalent. The production yield is represented by squares and the residual concentration of glycerol by circles. The results of the non-mutated strain NCYC 995 (control) are shown in white and those of the corresponding mutated strain I-3888 in black.

In FIGS. 5 and 6, each point corresponds to a steady state obtained with a feed medium in which the proportion of glycerol in the mixture of glycerol and sugar is 0%, 20%, 50% or 80% sugar equivalent.

With a feed medium the only carbon source of which is glucose (absence of glycerol), the biomass production yield of the mutated strain (CNCM I-3887) and that of the non-mutated strain (NCYC 996) are identical. The mutation of the STL1 gene does not therefore modify the biomass production yield on glucose.

Figure 7:
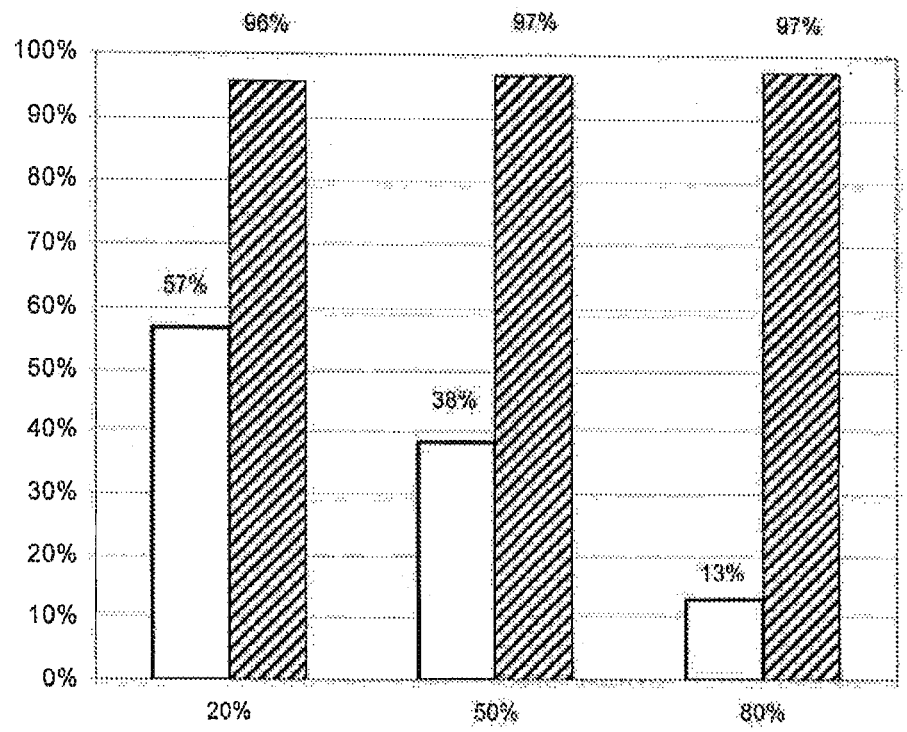
FIG. 7: Percentage of glycerol consumed after culture in chemostat mode of the strain I-3887 and of the strain NCYC 996, as a function of the proportion of glycerol in the mixture of glycerol and sugar in the feed medium. The percentage of glycerol consumed (on the y-axis) is given as a function of the proportion of glycerol in the mixture of glycerol and sugar as saccharose equivalent (on the x-axis). The percentage of glycerol consumed by the non-mutated strain NCYC 996 (control) is represented in white and that of the corresponding mutated strain I-3887 hatched.
Figure 8:
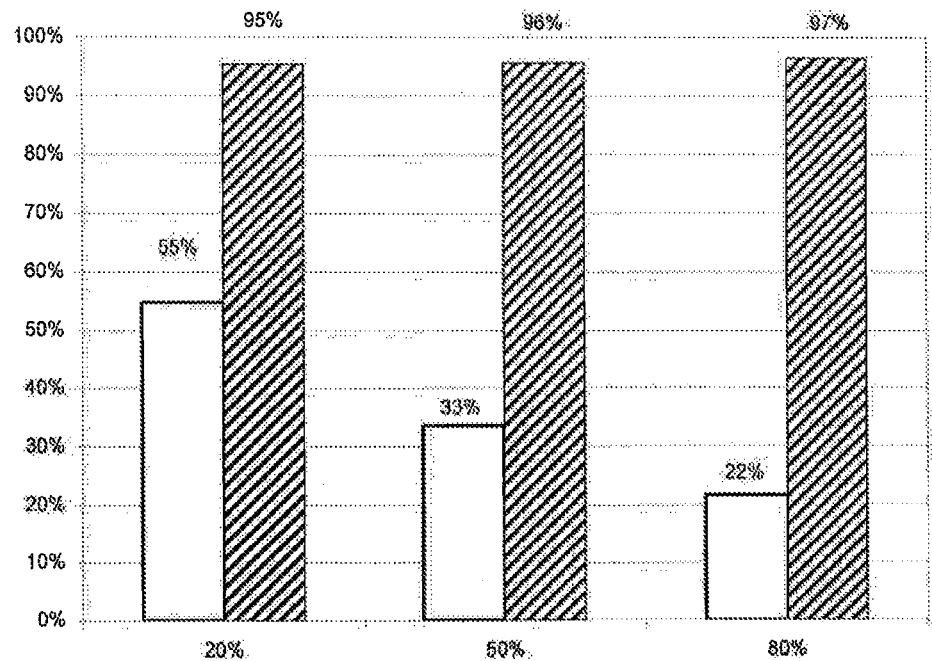
FIG. 8: Percentage of glycerol consumed after culture in chemostat mode of the strain I-3888 and of the strain NCYC 995, as a function of the proportion of glycerol in the mixture of glycerol and sugar in the feed medium. The percentage of glycerol consumed (on the y-axis) is given as a function of the proportion of glycerol in the mixture of glycerol and sugar as saccharose equivalent (on the x-axis). The percentage of glycerol consumed by the non-mutated strain NCYC 995 (control) is represented in white and that of the corresponding mutated strain I-3888 hatched.

The substitution of 20%, 50% or 80% of the glucose as saccharose equivalent by glycerol in the mixture of glycerol and sugar in the feed is accompanied, in the case of the non-mutated strain, by a growing accumulation of glycerol in the reaction medium (FIGS. 7 and 8). This quantity of glycerol which accumulates in the reaction medium leads to a marked reduction in the biomass production yield on poured sugar equivalent (FIGS. 5 and 6). Thus, at a 50% substitution level, the production yield of the non-mutated strains dropped by 25% in relation to the yield of the same strain produced on a medium containing only glucose.

The consumption of glycerol of the non-mutated strains is less than 57% at a 20% substitution level, less than 38% at a 50% substitution level and less than 22% at an 80% substitution level (FIGS. 7 and 8).

By contrast, the mutated strains consume virtually all of the glycerol supplied, simultaneously with the sugar, as shown by the very low concentration of residual glycerol measured in the reaction medium. Thus, the mutated strains consume more than 95% of the glycerol in the mixture, up to an 80% substitution level (FIGS. 7 and 8). Consequently, the production yield on supplied sugar equivalent is not affected, or only slightly affected, by the level of substitution of glycerol for sugar. The production yield of the mutated strain is always greater than that of the corresponding non-mutated strain in the presence of a mixture containing glycerol (FIGS. 5 and 6).

Moreover, in the presence of a mixture of glycerol and sugar comprising 20% or 50% glycerol as saccharose equivalent, the production yield of the mutated strains is greater than 90% in relation to that of the non-mutated strain cultured in the absence of glycerol, and it is greater than 85% in the presence of a mixture of glycerol and sugar comprising 80% glycerol as saccharose equivalent (FIGS. 5 and 6).

Example 3

Obtaining Natural Variants According to the Invention

Material and Methods
(i) Direct Screening

A population of cells of a strain of standard breadmaking yeast is subjected to UV radiation of 1200 to 2000 J/cm$^2$ leading to a 99.9% loss of viability.

The natural variants obtained are isolated on a non-selective medium (YPG), then screened on the basis of their yield and their consumption of glycerol in the presence of a mixture of glycerol and sugar.

The screening is carried out after culture in semi-continuous mode, in the presence of a mixture of glycerol and sugar comprising 20% glycerol as saccharose equivalent, in 1-liter, then 7-liter fermenters.

The experimental conditions of the semi-continuous culture are as described in Example 2 over a period of 22 hours, with an average growth rate of 0.16 h$^-$.

(ii) Screening after Chemostat Enrichment

A population of cells of the same starting strain as previously is subjected to increasing levels of UV radiation (from 400 to 4400 J/cm$^2$) leading to losses of viability ranging from 80 to 99.98%.

The natural variants subjected to these different radiation levels are then combined and a part is used for seeding a culture in chemostat mode.

The source of carbon of the culture is constituted by a mixture of glycerol and glucose comprising 50% glycerol as saccharose equivalent.

The culture is carried out until approximately 220 cell generations are obtained.

The consumption of glycerol is measured during the culture.

Samples of the culture are taken regularly for screening of the natural variants.

The natural variants originating from the different samples are isolated on a non-selective medium (YPG), then screened on the basis of their yield and their consumption of glycerol in the presence of a mixture of glycerol and sugar.

The screening is carried out after culture in semi-continuous mode, in the presence of a mixture of glycerol and sugar comprising 20% glycerol as saccharose equivalent, in 1-liter, then 7-liter fermenters.

The experimental conditions of the semi-continuous culture are as described in Example 2 over a period of 22 hours, with an average growth rate of 0.16.

Results

The natural variants originating from direct screening or from screening after chemostat enrichment exhibit very varied glycerol consumption and yield profiles.

Figure 9:
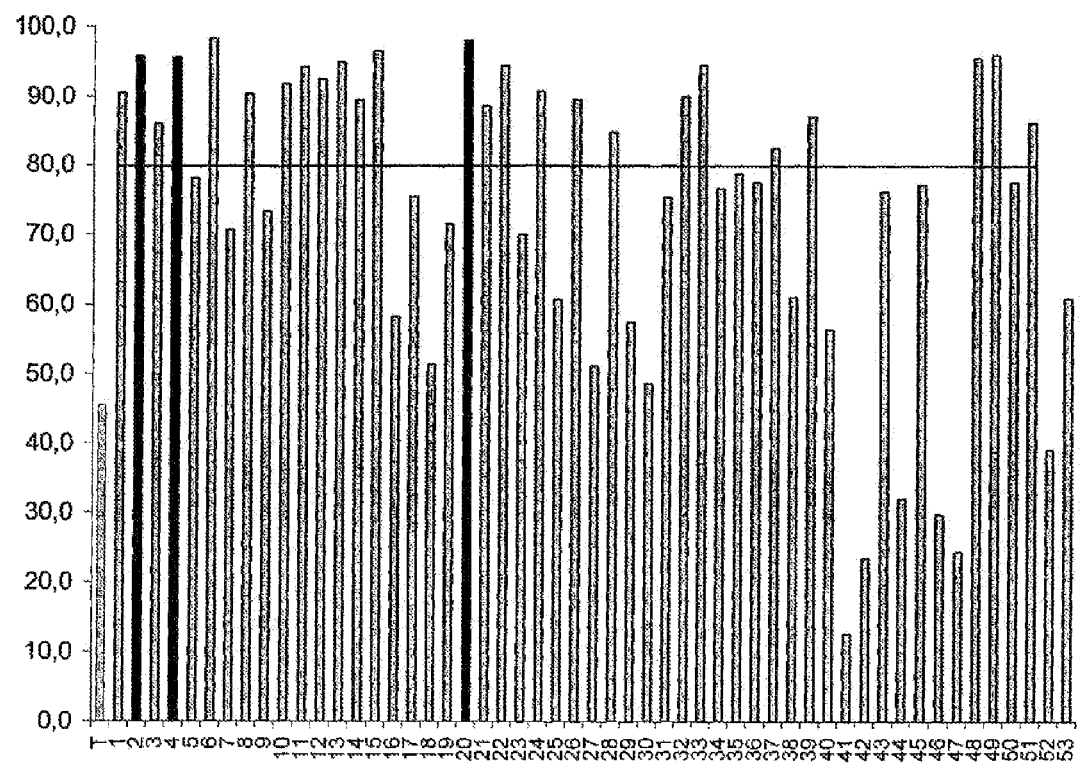
FIG. 9: Percentage of glycerol consumed after culture in semi-continuous mode of natural variants in the presence of a mixture of glycerol and sugar comprising 20% glycerol as saccharose equivalent.
The percentage of glycerol consumed (on the y-axis) is indicated for different natural variants tested (1 to 53). The percentage of glycerol consumed by the non-mutated strain from which the natural variants (denoted T) are obtained is also indicated.

An example of a result obtained on 53 natural variants originating from screening after chemostat enrichment is shown in FIG. 9. The glycerol consumption of the starting strain (T) is also indicated.

A certain number of natural variants exhibit a glycerol consumption greater than 80% in the presence of a mixture of glycerol and sugar comprising 20% glycerol as saccharose equivalent and a yield greater than or equal to 85% of the starting strain.

These include the natural variants deposited at the CNCM under numbers I-4129 (natural variant no. 4), I-4130 (natural variant no. 20) and I-4131 (natural variant no. 2) which were obtained by screening after chemostat enrichment from the sampling corresponding to the obtaining of approximately 145 cell generations in the chemostat.

It is noted that the analysis of the glycerol consumption during the culture in the chemostat shows that during the first 100 generations, the residual glycerol reduces regularly, which suggests an adaptation of the culture to the mixture of glycerol and sugar.

Moreover, the mRNA level corresponding to the transcription of the STL1 gene is measured by quantitative RT-PCR, as indicated in Example 1, on different natural variants according to the invention. The mRNA level obtained is then compared to that of the starting strain which has not undergone UV treatment.

Depending on the natural variants, an mRNA level is observed similar to that of the starting strain or multiplied by a factor of 2 to a factor of 7.

The ability of the strains according to the invention to consume glycerol in the presence of a mixture of glycerol and sugar is therefore not necessarily linked to an overexpression of the STL1 gene.

Example 4

Production of Yeasts from Natural Variants According to the Invention on a Mixture of Glycerol and Sugar Material and Methods The cultures in semi-continuous mode are carried out as in Example 2, over a period of 22 hours, with an average growth rate of 0.16 h$^{-1}$.

Results

The natural variants I-4129, I-4130, and I-4131, as well as the starting strain of yeast from which they originate are produced according to the procedure described above, with pure molasses or a mixture of glycerol and molasses comprising a proportion of glycerol of 20% or 40% as saccharose equivalent as a source of carbon.

The production yield is determined for the starting strain in the presence of pure molasses (without glycerol). In Tables 6 and 7, the values shown on the line "yield" correspond to the percentage yield in relation to the yield of the starting strain produced on pure molasses.

Tables 6 and 7 indicate the results of the tests carried out with the natural variants and the starting strain (T) in the presence of a mixture of glycerol and sugar comprising 20% and 40% glycerol respectively.

TABLE 6

| | 0% glycerol | 20% glycerol | | |
|---|---|---|---|---|
| | T | T | I-4129 | I-4130 | I-4131 |
| Yield (as a percentage of the yield of the control strain in the absence of glycerol) | 100.0 | 86.5 | 98.9 | 100.3 | 100.6 |
| Supplied glycerol consumed (in %) | / | 38.5 | 99.6 | 99.6 | 99.5 |

TABLE 7

| | 0% glycerol | 40% glycerol | | |
|---|---|---|---|---|
| | T | I-4129 | I-4130 | I-4131 |
| Yield (as a percentage of the yield of the control strain in the absence of glycerol) | 100.0 | 99.7 | 88.2 | 93.5 |
| Supplied glycerol consumed (in %) | / | 99.1 | 85.6 | 93.1 |

The measurements carried out indicate that the consumption of the glycerol supplied is practically total for the three natural variants in the presence of a mixture of glycerol and sugar comprising 20% glycerol as saccharose equivalent (consumption of glycerol greater than 99%), whereas the consumption of the starting strain is less than 40% (Table 6).

In the presence of a mixture of glycerol and sugar comprising 40% glycerol as saccharose equivalent, the measurements carried out indicate that the consumption of the glycerol supplied is practically total for the natural variant I-4129, greater than 85% for the natural variant I-4130 and greater than 90% for the variant I-4131.

The invention claimed is:

1. A strain of *Saccharomyces*, wherein said strain is chosen from the group consisting of:
    an isolated pure strain deposited at the Collection Nationale de Cultures de Microorganismes (CNCM) on 20 Dec. 2007 under number I-3886,
    an isolated pure strain deposited at the CNCM on 20 Dec. 2007 under number I-3887,
    an isolated pure strain deposited at the CNCM on 20 Dec. 2007 under number I-3888,
    an isolated pure strain deposited at the CNCM on 3 Mar. 2009 under number I-4132, and
    an isolated pure strain deposited at the CNCM on 3 Mar. 2009 under number I-4133.

2. A method of multiplying the strain of claim 1, comprising the steps of:
    introducing the strain into a fermentation vessel, and
    multiplying said strain under aerobic conditions according to a semi-continuous mode or according to a continuous mode in a culture medium comprising a mixture of glycerol and other sugars, said mixture comprising a proportion of glycerol of at least 5% as saccharose equivalent, the sum of the proportion of glycerol and sugar in said mixture being equal to 100% as saccharose equivalent.

3. The method according to claim 2, wherein said mixture comprises a proportion of glycerol of at least 8% as saccharose equivalent.

4. The method according to claim 2, wherein said mixture comprises a proportion of glycerol of at least 30% as saccharose equivalent.

5. The method according to claim 2, wherein said mixture comprises a proportion of glycerol of at least 40% as saccharose equivalent.

6. The method according to claim 2, wherein said mixture comprises a proportion of glycerol of at least 50% as saccharose equivalent.

7. The method according to claim 2, wherein said mixture comprises a proportion of glycerol of at least 60% as saccharose equivalent.

8. The method according to claim 2, wherein said mixture comprises a proportion of glycerol of at least 70% as saccharose equivalent.

9. The method according to claim 2, wherein said mixture comprises a proportion of glycerol of at least 80% as saccharose equivalent.

10. The method according to claim 2, wherein said mixture comprises a proportion of glycerol of at least 90% as saccharose equivalent.

* * * * *